United States Patent
Itkowitz et al.

(10) Patent No.: US 11,992,283 B2
(45) Date of Patent: May 28, 2024

(54) SYSTEMS AND METHODS FOR CONTROLLING TOOL WITH ARTICULATABLE DISTAL PORTION

(71) Applicant: INTUITIVE SURGICAL OPERATIONS, INC., Sunnyvale, CA (US)

(72) Inventors: Brandon D. Itkowitz, San Jose, CA (US); David W. Robinson, Los Altos, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 612 days.

(21) Appl. No.: 16/489,735

(22) PCT Filed: Mar. 7, 2018

(86) PCT No.: PCT/US2018/021373
§ 371 (c)(1),
(2) Date: Aug. 29, 2019

(87) PCT Pub. No.: WO2018/165320
PCT Pub. Date: Sep. 13, 2018

(65) Prior Publication Data
US 2019/0380798 A1    Dec. 19, 2019

Related U.S. Application Data

(60) Provisional application No. 62/468,097, filed on Mar. 7, 2017.

(51) Int. Cl.
*A61B 34/35* (2016.01)
*A61B 1/00* (2006.01)
(Continued)

(52) U.S. Cl.
CPC .......... *A61B 34/35* (2016.02); *A61B 1/00149* (2013.01); *A61B 1/3132* (2013.01);
(Continued)

(58) Field of Classification Search
CPC ............ A61B 2034/2065; A61B 34/35; A61B 1/00149; A61B 1/3132;
(Continued)

(56) References Cited

U.S. PATENT DOCUMENTS 5,524,180 A * 6/1996 Wang .................. B60R 21/0132
600/117
5,836,869 A * 11/1998 Kudo ..................... A61B 34/20
600/173
(Continued)

FOREIGN PATENT DOCUMENTS

CN   105407817 A   3/2016
EP   2889015 A1    7/2015
(Continued)

OTHER PUBLICATIONS

Extended European Search Report for Application No. 18764618.7, dated Feb. 13, 2020, 8 pages.
(Continued)

*Primary Examiner* — Anh Tuan T Nguyen
*Assistant Examiner* — Shankar Raj Ghimire
(74) *Attorney, Agent, or Firm* — Haynes & Boone, LLP.

(57) ABSTRACT

A system comprises a medical tool including a shaft having proximal and distal ends and an articulatable distal portion coupled to the distal end of the shaft. The system also comprises a processing unit including one or more processors. The processing unit is configured to determine a target in a medical environment. The articulatable distal portion is directed toward the target. The processing unit is also configured to determine a motion of at least a portion of the
(Continued)

shaft, and in response to the determined motion, control a pose of the articulatable distal portion so that the articulatable distal portion remains directed toward the target.

16 Claims, 16 Drawing Sheets

(51) Int. Cl.
  *A61B 1/313* (2006.01)
  *A61B 34/20* (2016.01)
  *A61B 17/00* (2006.01)
(52) U.S. Cl.
  CPC . *A61B 1/00193* (2013.01); *A61B 2017/00314* (2013.01); *A61B 2034/2065* (2016.02)
(58) Field of Classification Search
  CPC ........... A61B 2017/00314; A61B 2017/00694; A61B 2034/2051; A61B 2034/2068
  See application file for complete search history.

(56) References Cited

U.S. PATENT DOCUMENTS

| | | | | |
|---|---|---|---|---|
| 6,470,236 | B2 * | 10/2002 | Ohtsuki | B25J 9/1689 600/595 |
| 6,471,637 | B1 * | 10/2002 | Green | A61B 1/00045 600/137 |
| 6,714,841 | B1 * | 3/2004 | Wright | A61B 90/36 600/407 |
| 6,843,793 | B2 | 1/2005 | Brock et al. | |
| 7,006,895 | B2 | 2/2006 | Green | |
| 7,876,942 | B2 * | 1/2011 | Gilboa | G06T 7/73 382/128 |
| 8,918,211 | B2 | 12/2014 | Diolaiti et al. | |
| 9,179,832 | B2 | 11/2015 | Diolaiti | |
| 9,381,010 | B2 * | 7/2016 | Hartoumbekis . | A61B 17/00234 |
| 10,251,532 | B2 * | 4/2019 | Schara | A61B 90/50 |
| 10,660,715 | B2 * | 5/2020 | Dozeman | B25J 9/1694 |
| 10,863,884 | B2 * | 12/2020 | Nakamura | A61B 1/00045 |
| 2001/0025183 | A1 * | 9/2001 | Shahidi | A61B 90/36 606/130 |
| 2003/0013949 | A1 * | 1/2003 | Moll | G16H 40/63 600/407 |
| 2003/0045778 | A1 * | 3/2003 | Ohline | A61B 1/31 600/114 |
| 2003/0055410 | A1 | 3/2003 | Evans et al. | |
| 2005/0123179 | A1 * | 6/2005 | Chen | G06T 3/60 382/128 |
| 2005/0154260 | A1 * | 7/2005 | Schara | A61B 1/04 600/173 |
| 2006/0189842 | A1 | 8/2006 | Hoeg et al. | |
| 2007/0013336 | A1 * | 1/2007 | Nowlin | B25J 9/1689 318/568.21 |
| 2007/0250113 | A1 * | 10/2007 | Hegeman | H04W 24/08 606/207 |
| 2007/0270686 | A1 | 11/2007 | Ritter et al. | |
| 2008/0208041 | A1 * | 8/2008 | Gilboa | A61B 6/12 600/426 |
| 2009/0062604 | A1 | 3/2009 | Minosawa et al. | |
| 2009/0088634 | A1 * | 4/2009 | Zhao | A61B 1/00193 600/425 |
| 2009/0088773 | A1 * | 4/2009 | Zhao | A61B 34/37 606/130 |
| 2009/0088897 | A1 * | 4/2009 | Zhao | A61B 34/30 700/250 |
| 2009/0248036 | A1 * | 10/2009 | Hoffman | A61B 1/045 606/130 |
| 2010/0331855 | A1 * | 12/2010 | Zhao | A61B 34/30 606/130 |
| 2012/0071794 | A1 | 3/2012 | Karni | |
| 2013/0331687 | A1 * | 12/2013 | Liao | A61B 6/487 600/424 |
| 2014/0222021 | A1 * | 8/2014 | Diolaiti | A61B 34/30 606/130 |
| 2014/0257329 | A1 | 9/2014 | Jang et al. | |
| 2014/0375784 | A1 * | 12/2014 | Massetti | G02B 23/2484 348/222.1 |
| 2015/0005576 | A1 * | 1/2015 | Belson | A61B 5/065 600/103 |
| 2015/0100069 | A1 * | 4/2015 | Inoue | A61B 90/50 606/130 |
| 2015/0342442 | A1 * | 12/2015 | Tadano | A61B 1/00006 600/102 |
| 2016/0037998 | A1 * | 2/2016 | Kawashima | A61B 1/04 600/102 |
| 2016/0101263 | A1 * | 4/2016 | Blumenkranz | A61B 5/065 600/117 |
| 2016/0128553 | A1 * | 5/2016 | Geng | A61B 1/05 600/111 |
| 2016/0213364 | A1 * | 7/2016 | Inoue | A61B 1/008 |
| 2016/0302653 | A1 * | 10/2016 | Inoue | A61B 1/00009 |
| 2016/0324399 | A1 * | 11/2016 | Banju | G02B 23/2484 |
| 2016/0353970 | A1 * | 12/2016 | Inoue | A61B 1/00009 |
| 2017/0135557 | A1 | 5/2017 | Inoue | |
| 2018/0214014 | A1 | 8/2018 | Diolaiti | |
| 2019/0125480 | A1 * | 5/2019 | Bernstein | A61B 34/35 |
| 2019/0151032 | A1 | 5/2019 | Mustufa et al. | |
| 2019/0159661 | A1 * | 5/2019 | Itkowitz | A61B 1/00149 |
| 2019/0159860 | A1 * | 5/2019 | Teranuma | A61B 1/00009 |
| 2019/0183321 | A1 * | 6/2019 | Teranuma | H04N 23/555 |
| 2019/0328474 | A1 * | 10/2019 | Popovic | A61B 34/70 |
| 2020/0085506 | A1 * | 3/2020 | Holthuizen | A61B 17/7032 |

FOREIGN PATENT DOCUMENTS

| | | | | |
|---|---|---|---|---|
| EP | | 2666433 | B1 * | 9/2015 ............. A61B 34/10 |
| EP | | 3025658 | A1 | 6/2016 |
| JP | | H08280695 | A | 10/1996 |
| JP | | H10192233 | A | 7/1998 |
| WO | WO-2006076789 | A1 * | 7/2006 | ............... A61B 5/06 |
| WO | WO-2007097034 | A1 | 8/2007 | |
| WO | WO-2015142943 | A1 | 9/2015 | |
| WO | WO-2015142956 | A1 | 9/2015 | |
| WO | WO-2016149320 | A1 | 9/2016 | |
| WO | WO-2016164311 | A1 | 10/2016 | |
| WO | WO-2017014303 | A1 | 1/2017 | |
| WO | WO-2018013198 | A1 | 1/2018 | |
| WO | WO-2018013204 | A1 | 1/2018 | |

OTHER PUBLICATIONS

International Preliminary Report on Patentability for Application No. PCT/US2018/021373, dated Sep. 25, 2019, 8 pages.
International Search Report and Written Opinion for Application No. PCT/US2018/021373, dated Jun. 20, 2018, 11 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Office Action for Chinese Application No. CN20188004486, dated Jun. 24, 2022, 54 pages.
Office Action for Chinese Application No. CN20188004486, dated Feb. 8, 2023, 53 pages.
Office Action for Chinese Application No. CN20188004486, dated Jun. 25, 2023, 50 pages.

* cited by examiner

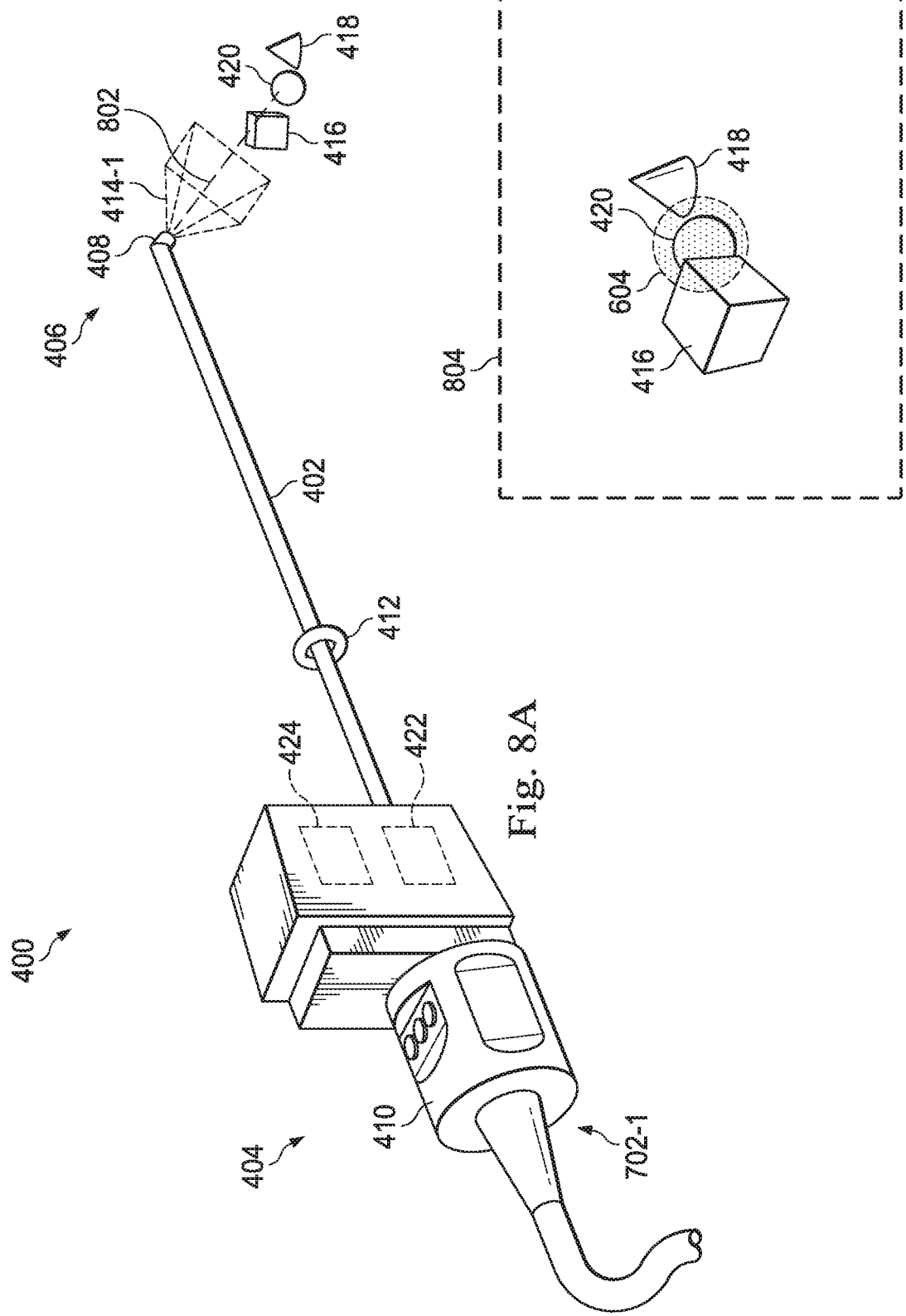

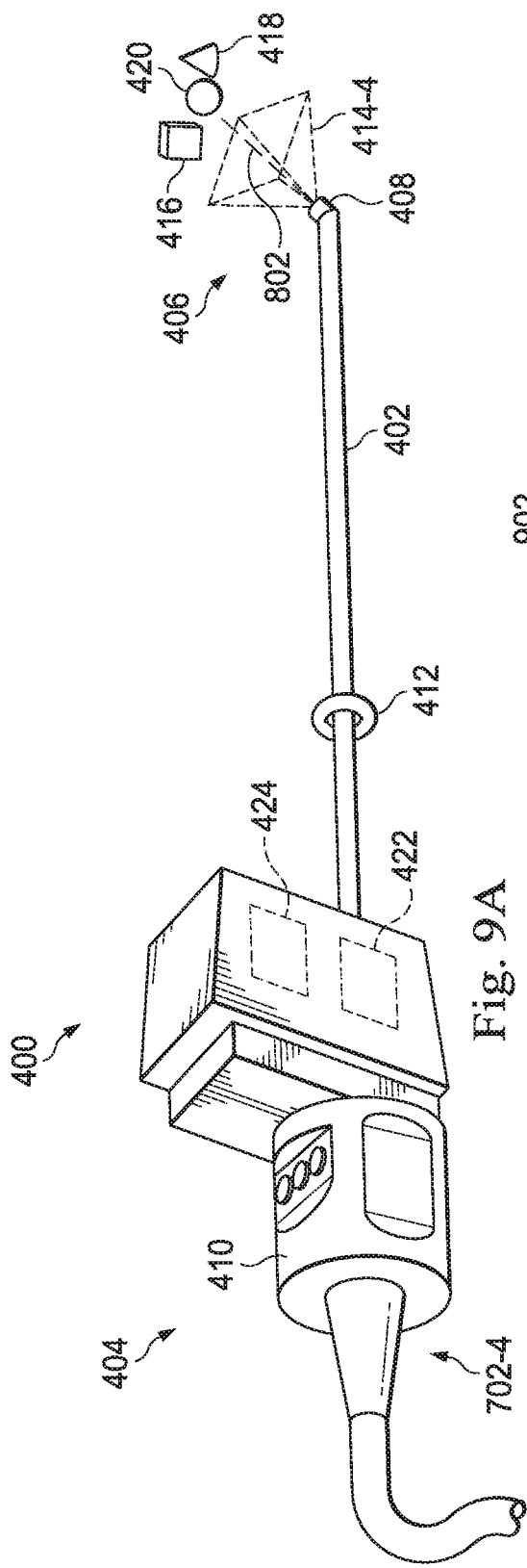
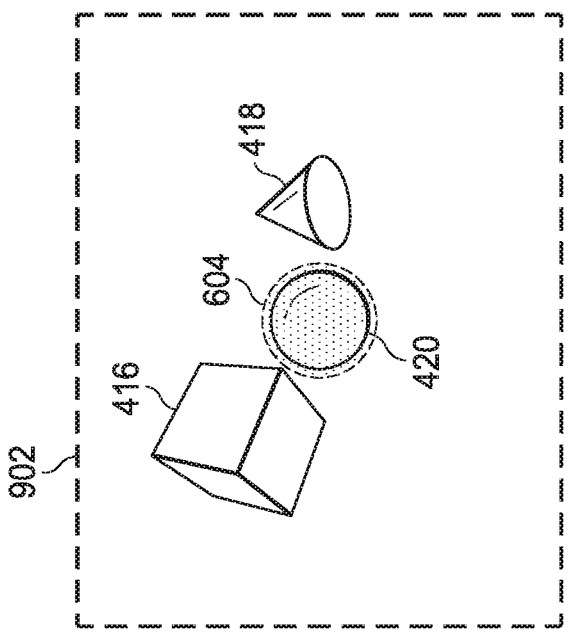
Fig. 9A
Fig. 9B

SYSTEMS AND METHODS FOR CONTROLLING TOOL WITH ARTICULATABLE DISTAL PORTION

CROSS-REFERENCE TO RELATED APPLICATIONS

This application claims priority to and benefit of the filing date of U.S. Provisional Patent Application No. 62/468,097, entitled "SYSTEMS AND METHODS FOR CONTROLLING MEDICAL TOOL WITH ARTICULATABLE DISTAL PORTION," filed Mar. 7, 2017, which is hereby incorporated by reference in its entirety.

FIELD

The present disclosure is directed to systems and methods for performing a procedure, and more particularly to systems and methods for controlling a tool with an articulatable distal portion.

BACKGROUND

Tools with articulatable distal portions can be used to manipulate and perform tasks in a work space. Such tools may be configured to be supported and operated manually, by robotic manipulator assemblies, or both manually or by robotic manipulator assemblies. For example, some tools comprise handheld devices with finger operated controls. As another example, some tools comprise interfaces to transmissions or actuators on manipulator assemblies. As a further example, some tools comprise both hand-operated controls and interfaces to robotic manipulator assemblies, and can interact with both simultaneously, or at different times.

Tools with articulatable distal portions can be used to perform non-medical and medical procedures. As a specific example, medical tools can be used to perform minimally invasive medical procedures. As another specific example, industrial tools can be used in manufacture or testing. As yet other examples, tools can be used in procedures for entertainment, exploration, and various other purposes.

Tools with articulatable distal portions can be complicated to control for a use. For example, some tools may be teleoperated or otherwise computer-assisted. When performing teleoperational procedures with remote instrument controllers, the proximal end of a tool may be moved for various reasons. For example, the proximal end of the tool may be moved side-to-side to avoid external collisions with other tools used in the teleoperational procedure. As a further example, the proximal end of the tool may be jostled due to unintentional movements of an operator of the tool. Such movements of the proximal end of the tool may cause unsteadiness, and cause unintentional changes to the orientation of a portion of the tool for which the operator wanted to maintain orientation. Example tool portions for which an operator may want to maintain orientation may include an end effector, an imager or other sensor, a distal tip of the tool, etc. In examples where the tool includes an imaging instrument, the proximal end of the tool may be moved (e.g., retracted, pivoted, inserted) to provide views of an object or region from various distances and directions. In such examples, movements of the proximal end of the tool may cause unsteadiness to the view and unintentional changes to the orientation of the field of view.

As a specific example for tools used in minimally invasive medical techniques, minimally invasive medical techniques are intended to reduce the amount of tissue that is damaged during invasive medical procedures. Such minimally invasive techniques may be performed through natural orifices in a patient anatomy or through one or more surgical incisions. Through these natural orifices or incisions, clinicians may insert medical tools to reach a target location, such as a target tissue location. Minimally invasive medical tools include instruments such as therapeutic instruments, diagnostic instruments, and surgical instruments. Minimally invasive medical tools may also include imaging instruments such as endoscopic instruments that provide a user with a field of view within the patient anatomy.

Thus, systems and methods are desired to provide better control of these tools, or of manipulator assemblies that support and operate these tools. These systems and methods may provide instrument stabilization and maintain the orientation of one or more portions of the tool in medical and non-medical contexts.

SUMMARY

The embodiments of the invention are summarized by the claims that follow below.

In one illustrative embodiment, a system comprises a tool, which could be a medical tool, including a shaft having proximal and distal ends and an articulatable distal portion coupled to the distal end of the shaft. The system also comprises a processing unit including one or more processors. The processing unit is configured to determine a target (such as a target object) in an environment (such as a medical environment), where the articulatable distal portion is directed toward the target. The processing unit is also configured to determine a first motion of at least a portion of the shaft, and in response to the determined first motion, control a pose of the articulatable distal portion so that the articulatable distal portion remains directed toward the target.

In another illustrative embodiment, a system comprises an imaging tool, which could be a medical imaging tool, including a shaft having proximal and distal ends and an articulatable distal portion coupled to the distal end of the shaft. The system also comprises a processing unit including one or more processors. The processing unit is configured to determine a target (such as a target object or other viewing target to be imaged by the imaging tool) in a field of view of the imaging tool. The processing unit is also configured to determine a first motion of the shaft, and in response to the determined first motion of the shaft, control a pose of the articulatable distal portion so that the target remains in the field of view of the imaging tool.

In another illustrative embodiment, a method comprises determining a target (such as a target object) in an environment (such a medical environment). The environment contains a medical tool, where an articulatable distal portion of the tool is directed toward the target. The tool includes a shaft having proximal and distal ends. The articulatable distal portion is coupled to the distal end of the shaft. The method also comprises determining a first motion of at least a portion of the shaft, and in response to the determined first motion, controlling a pose of the articulatable distal portion so that the articulatable distal portion remains directed toward the target.

In another illustrative embodiment, a method comprises determining a target (such as target object or other viewing target to be imaged by the imaging tool) in a field of view of an imaging tool, which could be a medical imaging tool. The imaging tool includes a shaft having proximal and distal ends and an articulatable distal portion coupled to the distal end of the shaft. The method also includes determining a motion of the shaft and in response to the determined motion of the shaft, controlling a pose of the articulatable distal portion so that the target remains in the field of view of the imaging tool.

In another illustrative embodiment, a non-transitory machine-readable medium comprises a plurality of machine-readable instructions which, when executed by one or more processors, are adapted to cause the one or more processors to perform a method. The method comprises determining a target (such as target object) in an environment (such as a medical environment.) The environment contains a tool, which could be a medical tool, associated with the one or more processors. An articulatable distal portion of the tool is directed toward the target. The tool includes a shaft having proximal and distal ends. The articulatable distal portion is coupled to the distal end of the shaft. The method also comprises determining a first motion of at least a portion of the shaft, and in response to the determined first motion, controlling a pose of the articulatable distal portion so that the articulatable distal portion remains directed toward the target.

In another illustrative embodiment, a non-transitory machine-readable medium comprising a plurality of machine-readable instructions which, when executed by one or more processors, are adapted to cause the one or more processors to perform a method. The method comprises determining a target (such as a target object or other viewing target to be imaged by the imaging tool) in a field of view of an imaging tool, which could be a medical imaging tool, associated with the one or more processors. The imaging tool includes a shaft having proximal and distal ends and an articulatable distal portion coupled to the distal end of the shaft. The method also comprises determining a motion of the shaft and in response to the determined motion of the shaft, controlling a pose of the articulatable distal portion so that the target remains in the field of view of the imaging tool.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 1 provides a view of a surgical environment in which a teleoperational medical system operates in accordance with an embodiment of the present disclosure.

Figure 6A:
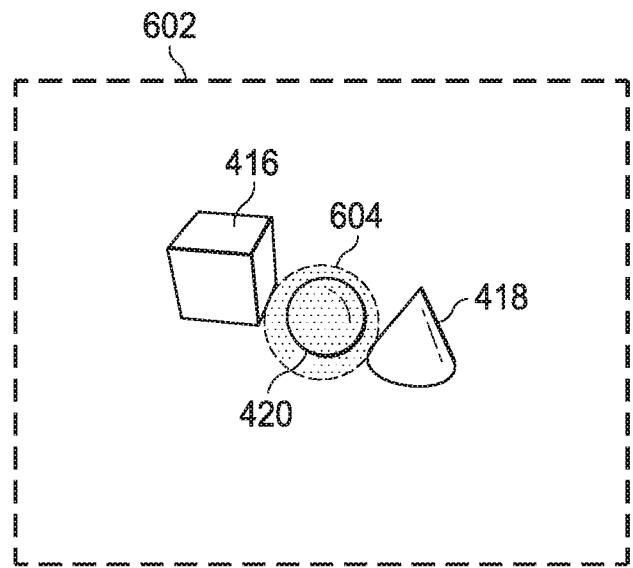
Figure 6B:
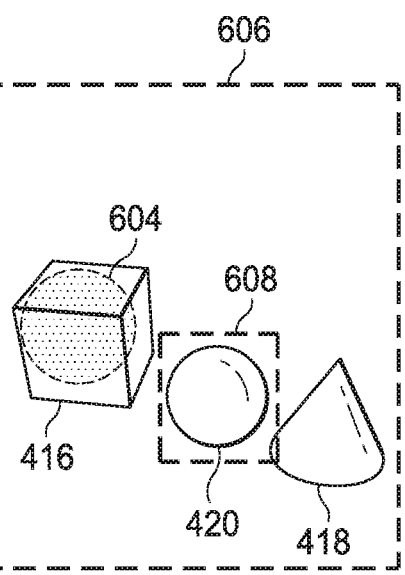
Figure 6C:
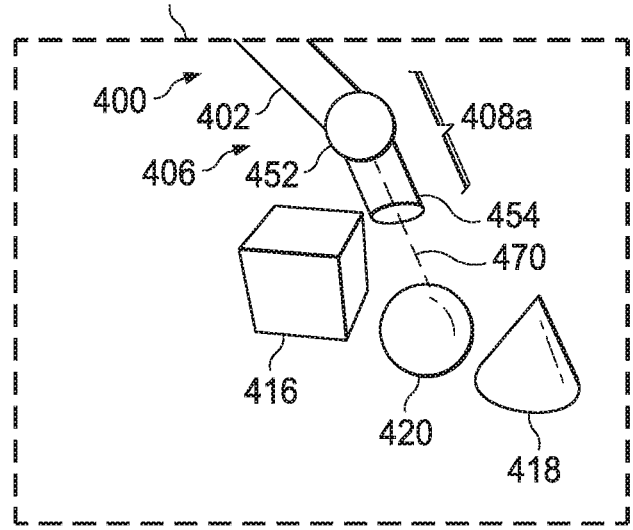

FIGS. 6A, 6B, and 6C illustrate imaging views for performing a targeting operation according to various embodiments of the present disclosure.

Figure 7:
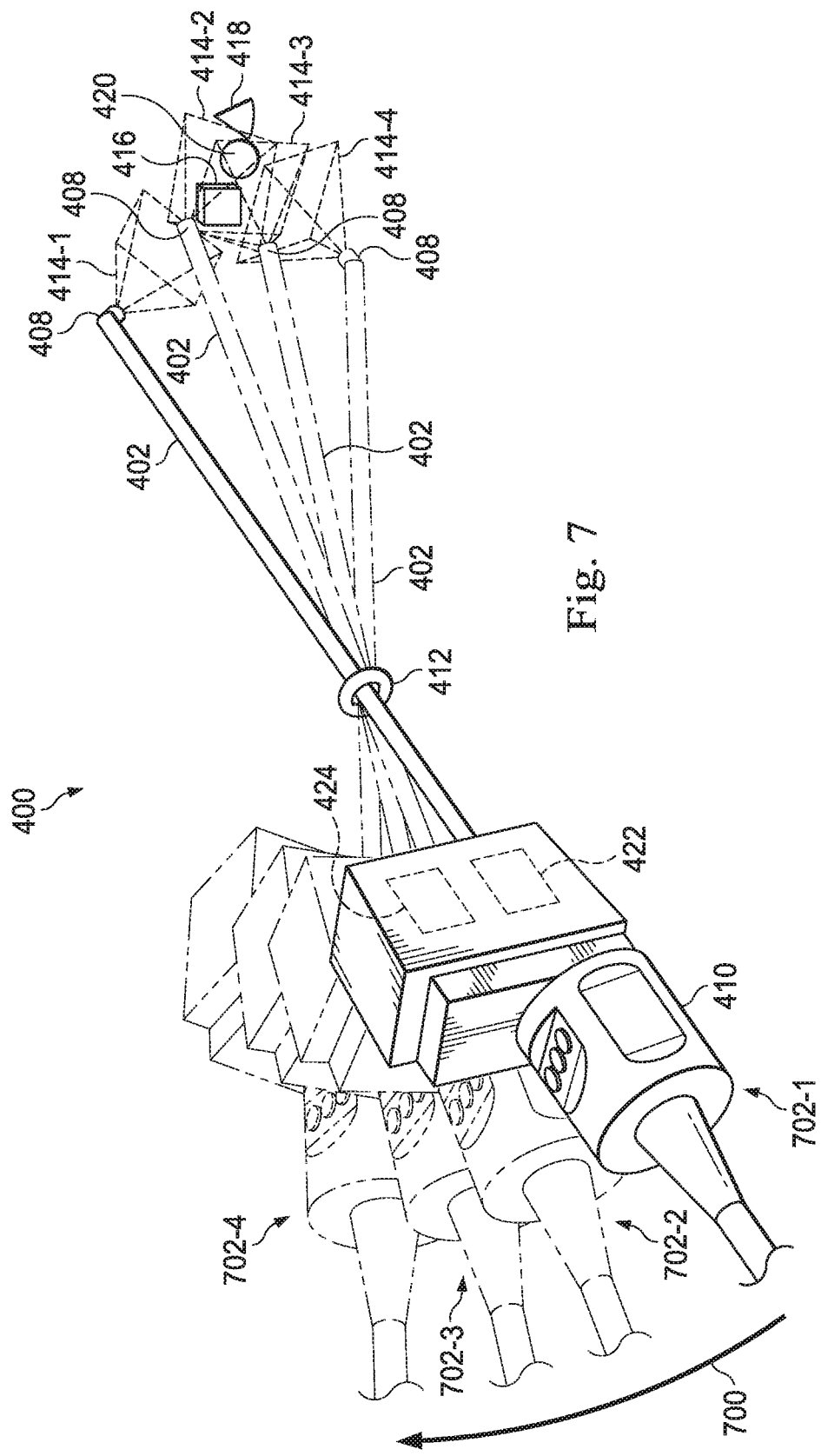

FIG. 7 is an illustration of a tool operating in a target tracking mode according to various embodiments of the present disclosure.

FIG. 8A illustrates a tool with its proximal end arranged at a first position according to an embodiment of the present disclosure. FIG. 8B illustrates the corresponding imaging view provided by the tool of FIG. 8A according to an embodiment of the present disclosure.

FIG. 9A illustrates a tool with its proximal end arranged at a second position according to an embodiment of the present disclosure. FIG. 9B illustrates the corresponding imaging view provided by the tool of FIG. 9A according to an embodiment of the present disclosure.

Figure 10A:
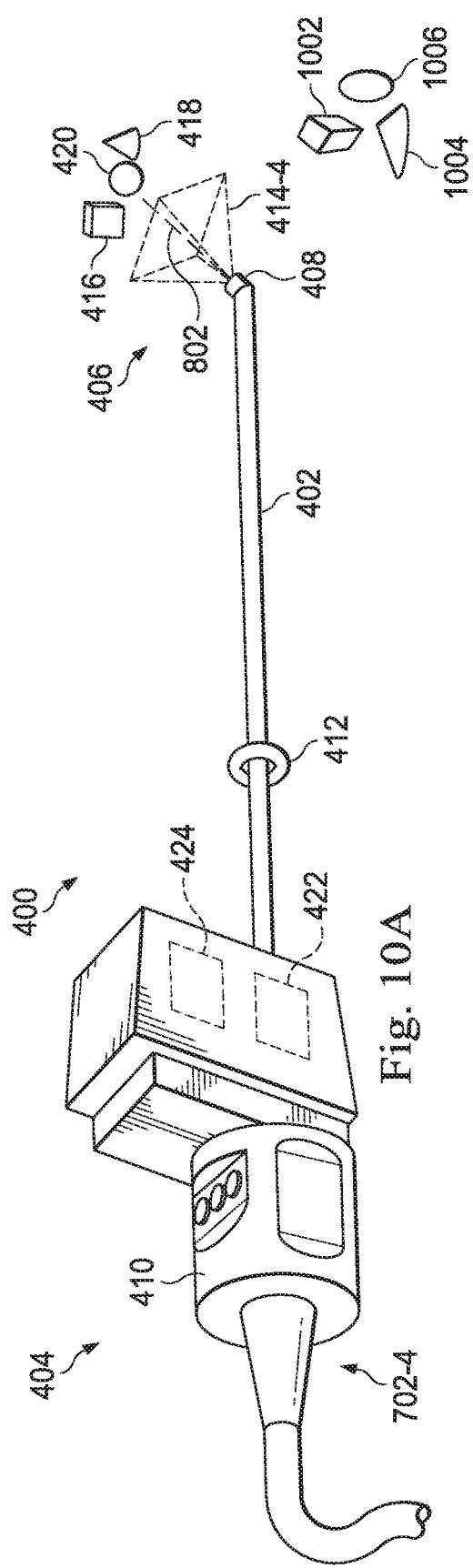
Figure 10B:
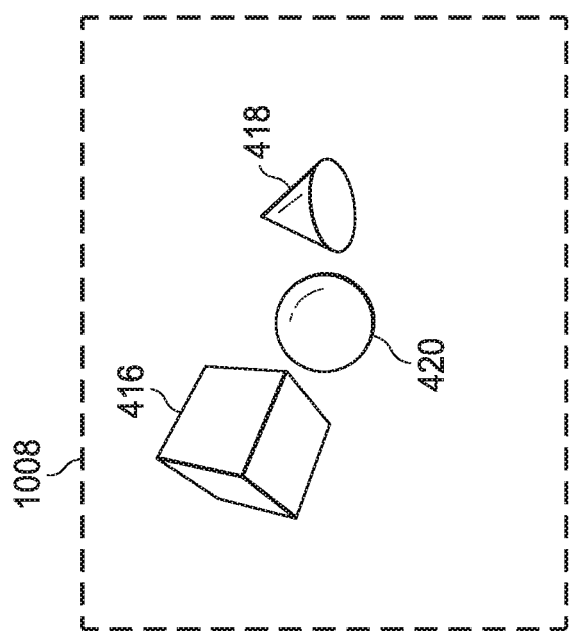

FIG. 10A illustrates a tool including an articulatable distal portion directed toward a first target according to an embodiment of the present disclosure. FIG. 10B illustrates the corresponding imaging view provided by the tool of FIG. 10A according to an embodiment of the present disclosure.

Figure 11A:
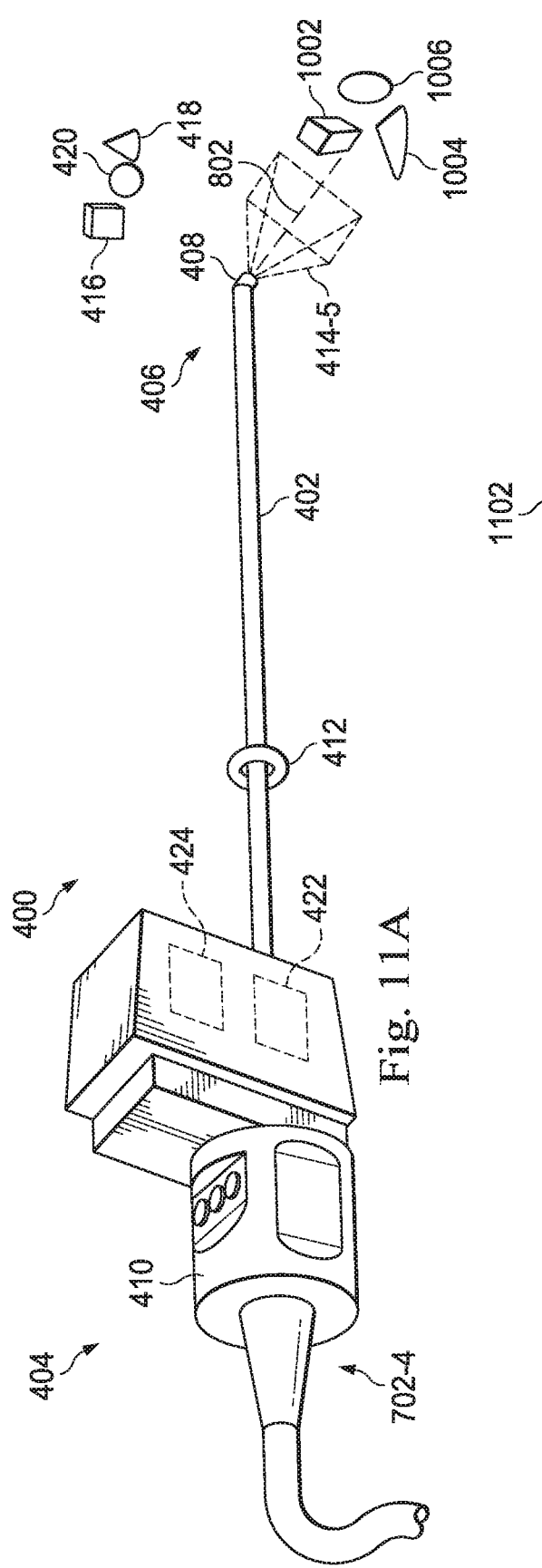
Figure 11B:
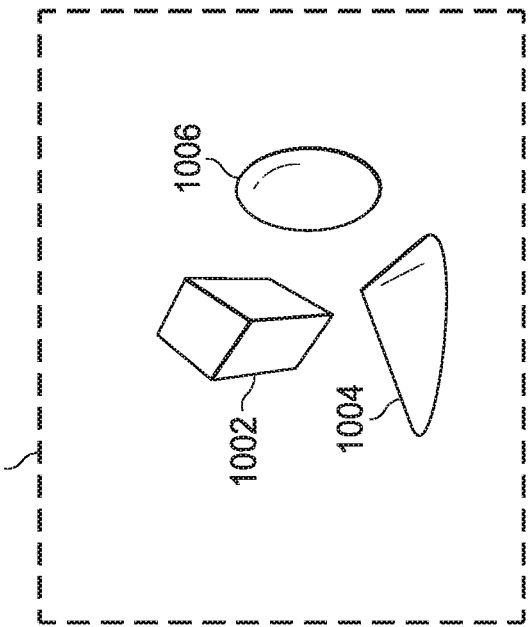

FIG. 11A illustrates a tool including an articulatable distal portion directed toward a second target according to an embodiment of the present disclosure. FIG. 11B illustrates the corresponding imaging view provided by the tool of FIG. 11A according to an embodiment of the present disclosure.

Figure 12:
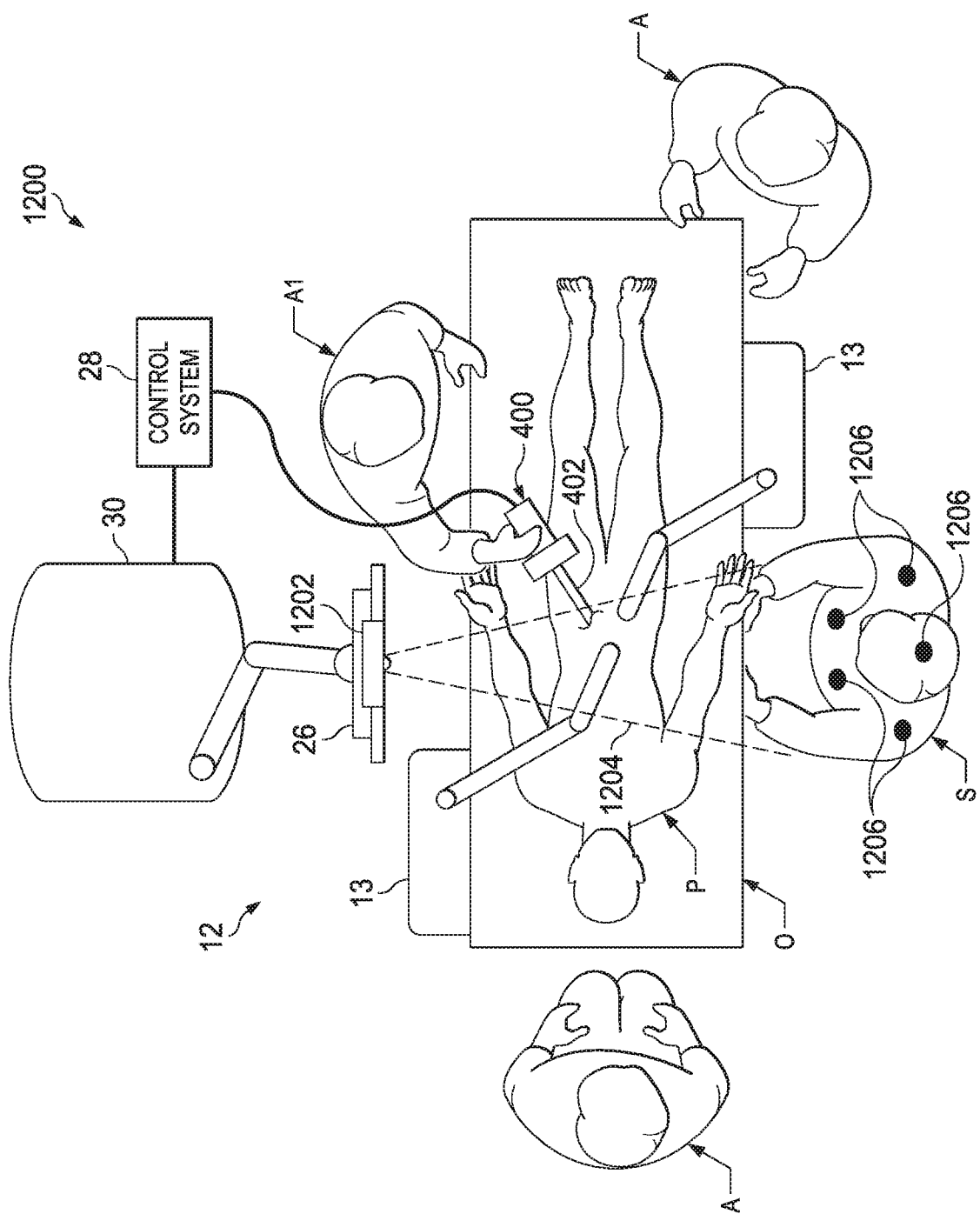

FIG. 12 illustrates a top view of a surgical environment in which a teleoperational medical system operates, where the teleoperational medical system includes a tracking system in accordance with an embodiment of the present disclosure.

Figure 13:
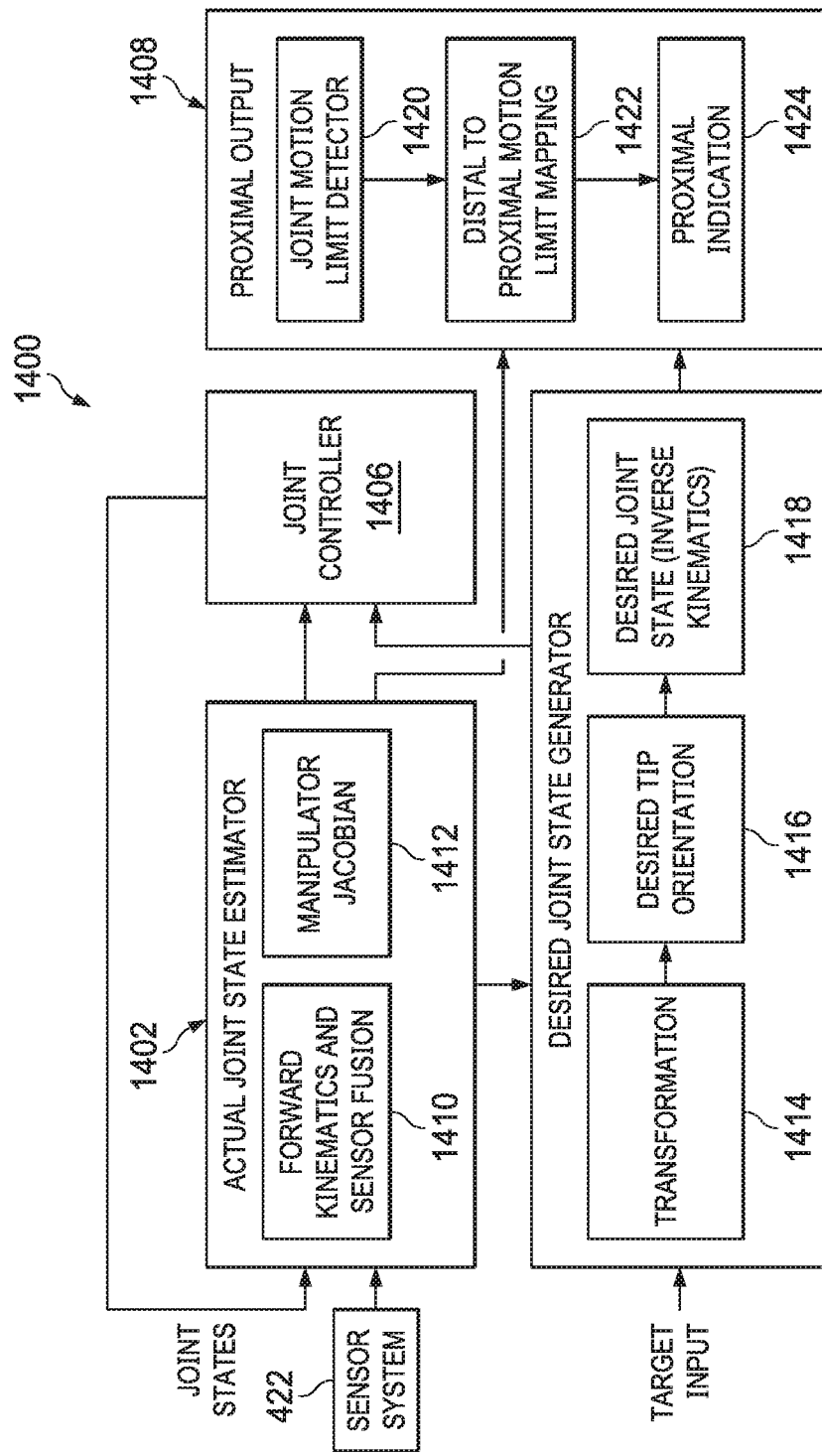

FIG. 13 illustrates a block diagram of a control system in accordance with an embodiment of the present disclosure.

Figure 14A:
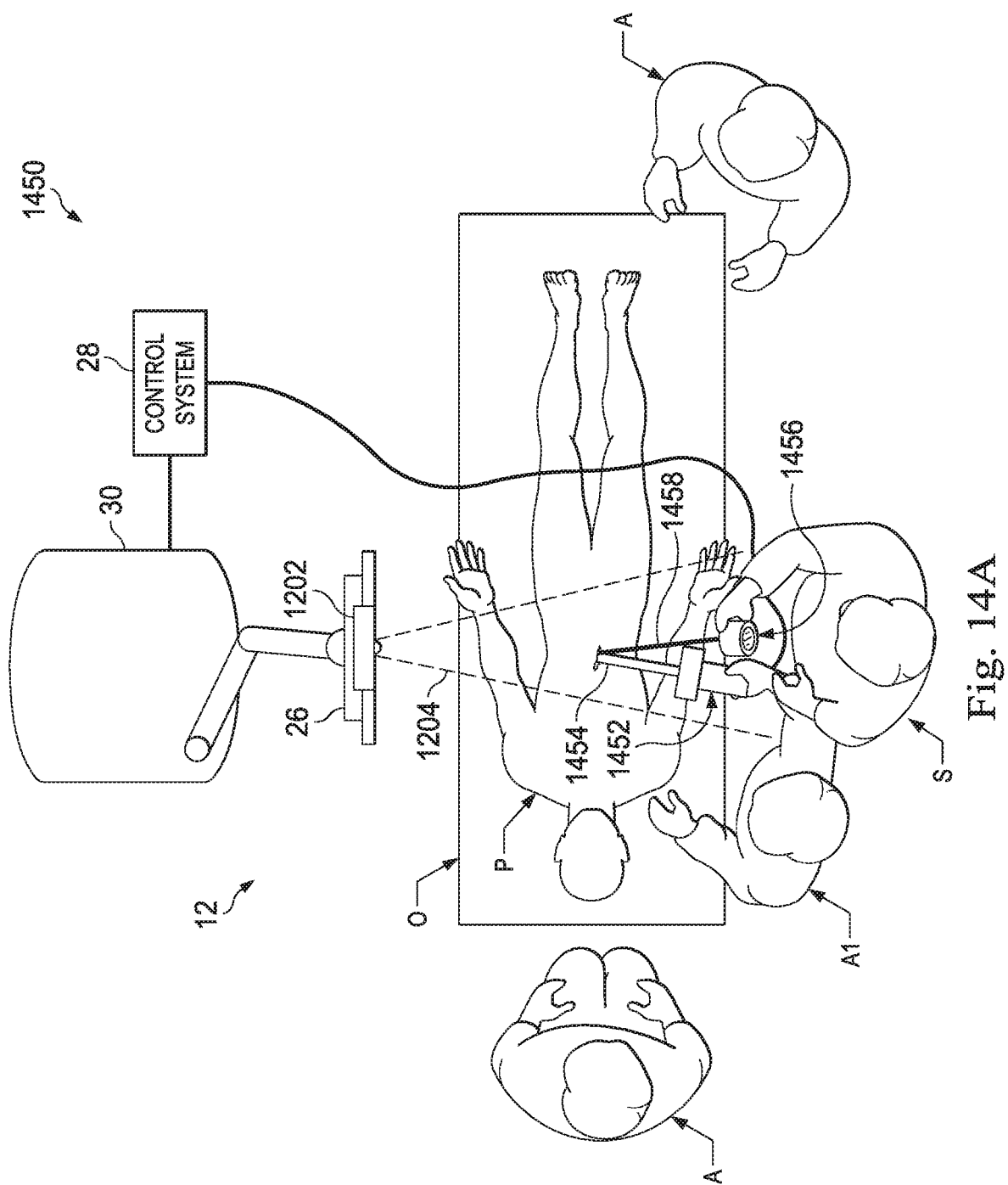
Figure 14B:
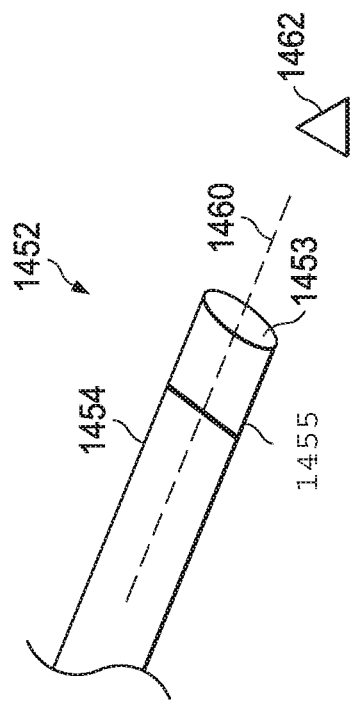

FIG. 14A illustrates a top view of a surgical environment in which a teleoperational medical system operates with a conventional imaging tool in accordance with an embodiment of the present disclosure. FIG. 14B illustrates the corresponding distal portion of the conventional imaging tool of FIG. 14A according to an embodiment of the present disclosure.

Figure 15B:
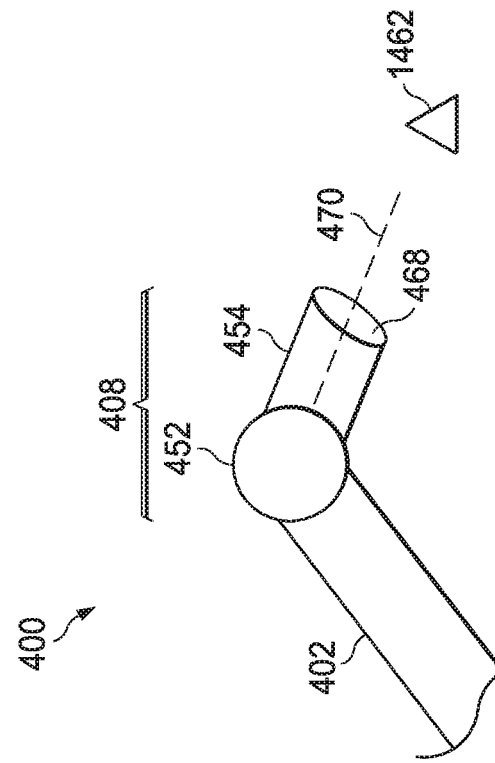
Figure 15A:
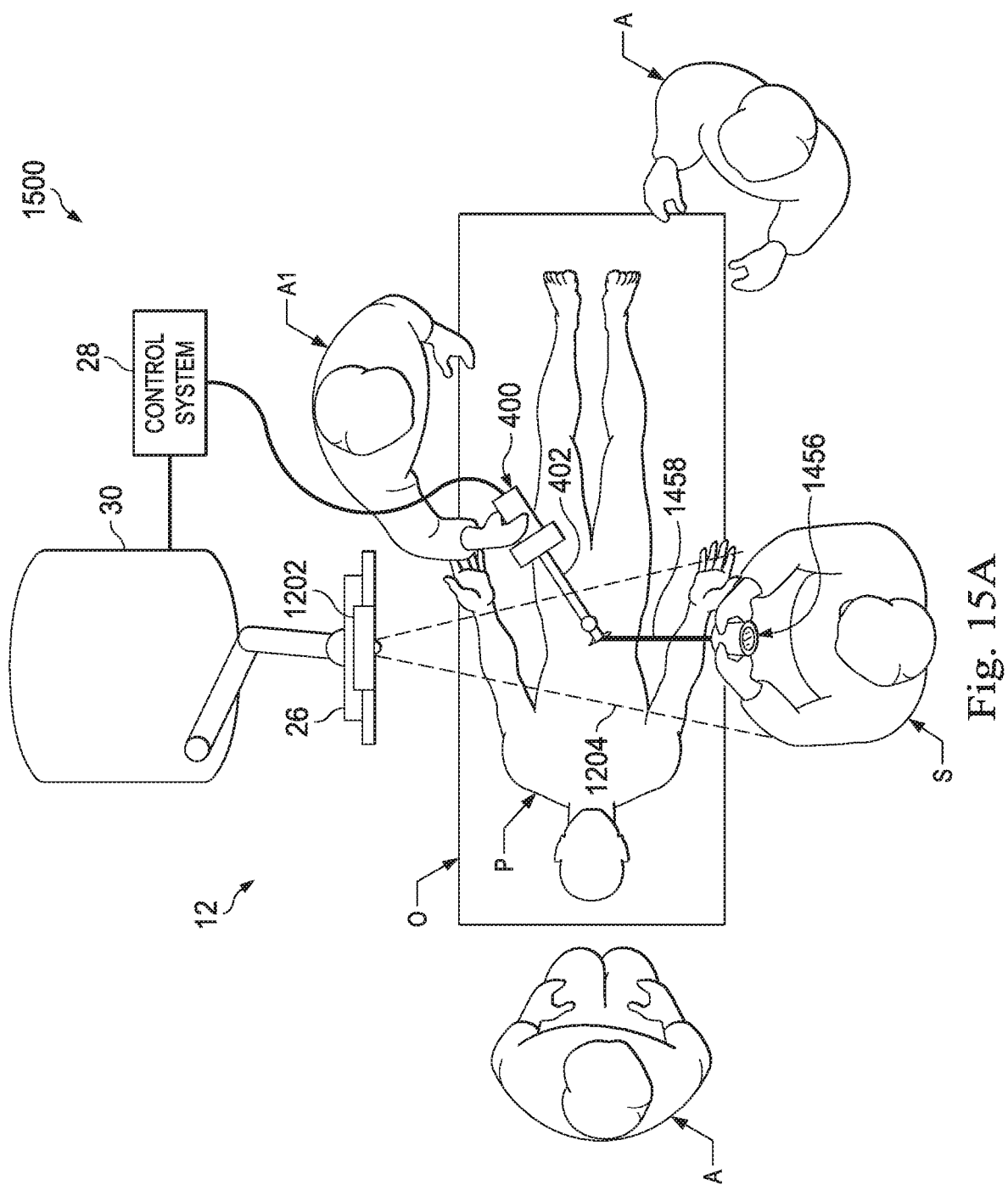

FIG. 15A illustrates a top view of a surgical environment in which a teleoperational medical system operates with an imaging tool with an articulatable distal portion in accordance with an embodiment of the present disclosure. FIG. 15B illustrates the corresponding articulatable distal portion of the imaging tool of FIG. 15A according to an embodiment of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well-known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location a three-dimensional space (e.g., three degrees of translational freedom that can be described using changes in Cartesian X, Y, Z coordinates, such as along Cartesian X, Y, Z axes). For example, the position may be of a point, a reference frame, an object, or a portion of an object. As used herein, the term "orientation" refers to the rotational placement (three degrees of rotational freedom— e.g., which can be described using roll, pitch, and yaw). For example, the orientation may be of a reference frame, an object, or a portion of an object. As used herein, the term "pose" refers to the position and the orientation. For example, the pose of a reference frame, an object, or a portion of an object would include both position and orientation information of such reference frame, object, or portion of the object. In a three-dimensional space, a full pose can be described with six mathematically independent degrees of freedom.

Also, although some of the examples described herein refer to surgical procedures or tools, or medical procedures and medical tools, the techniques disclosed apply to non-medical procedures and non-medical tools. For example, the tools, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy), and performing procedures on human or animal cadavers. Further, these techniques can also be used for surgical and nonsurgical, medical treatment or diagnosis procedures.

Figure 1:
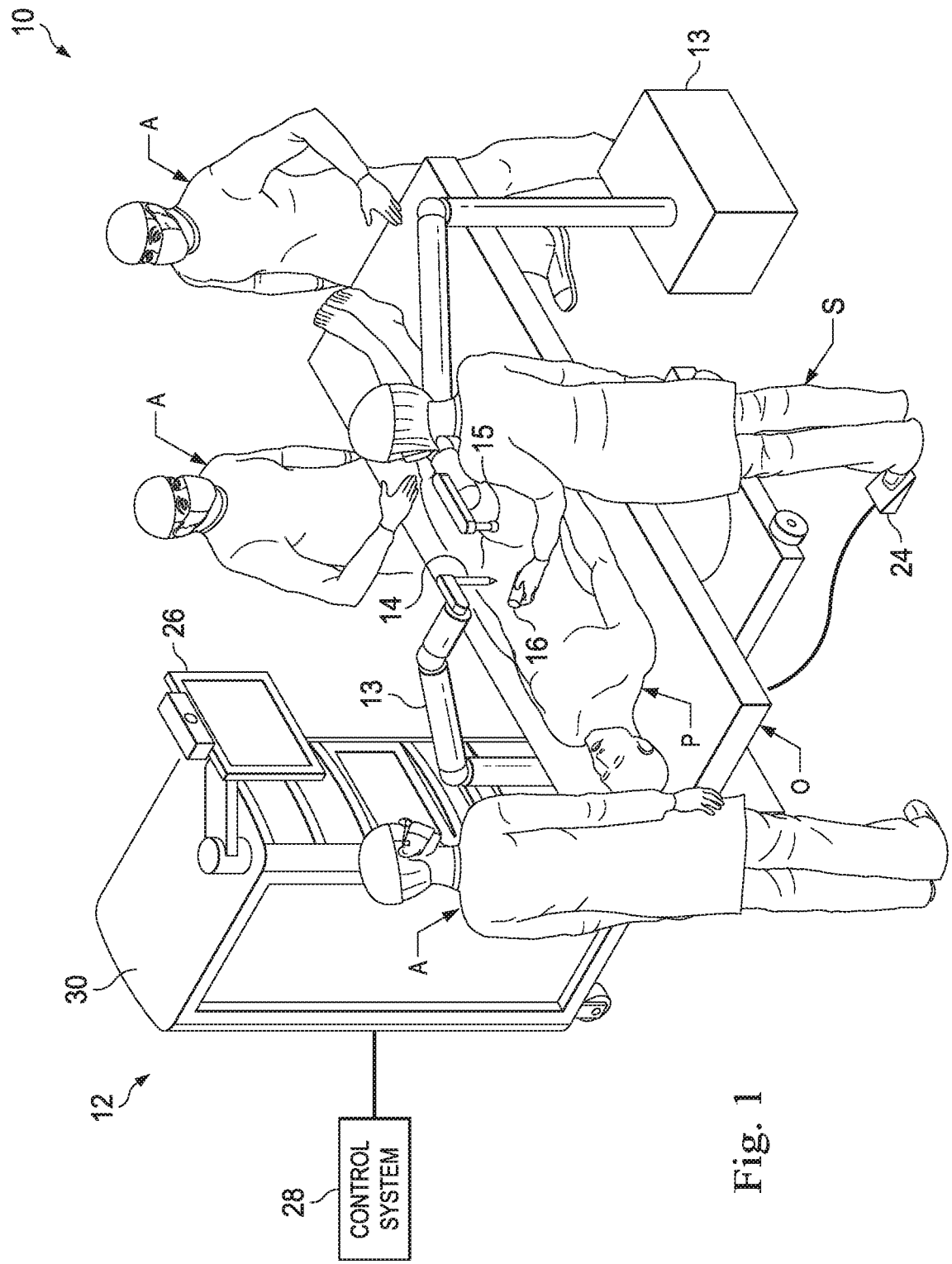

Referring to FIG. 1 of the drawings, an example medical environment with an exemplary system is shown. Specifically, FIG. 1 shows a surgical environment 10 that includes a teleoperational medical system 12 for use in, for example, medical procedures such as diagnostic, therapeutic, or surgical procedures. The surgical environment 10 can be described with a surgical coordinate space, and thus can be said to define the surgical coordinate space. The teleoperational medical system 12 generally includes a teleoperational assembly 13 mounted to or near an operating table O on which a patient P is positioned. The teleoperational assembly 13 may include one or more modular or integral manipulator arms. A medical instrument system 14 or an endoscopic imaging system 15 may be operably coupled to a teleoperational manipulator (e.g. an arm) of the teleoperational assembly 13. An operator input system 16 allows a surgeon (or other type of clinician or operator) S to control the operation of the medical instrument system 14 and/or the endoscopic imaging system. One or more assistant surgeons, anesthesiologists, or support personnel A may also be present in the surgical environment.

For simplicity of explanation, much of this application refers to the person S as a surgeon, and the person A as an assistant. However, it should be understood that, where specialized surgical or assistant skills are not required, the person S may be a surgeon, some other clinician, some other medical personnel, some non-medical operator, or some other person. Similarly, the person A may be an assistant surgeon, some other clinician, some other medical personnel, some non-medical operator, or some other person. Also, where the procedure performed is not on a patient (e.g. for an industrial application, for training, for work on a cadaver or anatomy removed from and not to be returned to a patient, etc.), the persons S and A may have little or no medical training or knowledge.

A display system 26 may present images captured by the endoscopic imaging system 15, surgical navigation and guidance images, and/or alphanumeric or symbolic information to assist the personnel with the surgical procedure. The teleoperational medical system 12 also includes a control system 28 (processing unit) in communication with the operator input system 16, the teleoperational assembly 13 and the display system 26, as described below.

Figure 2:
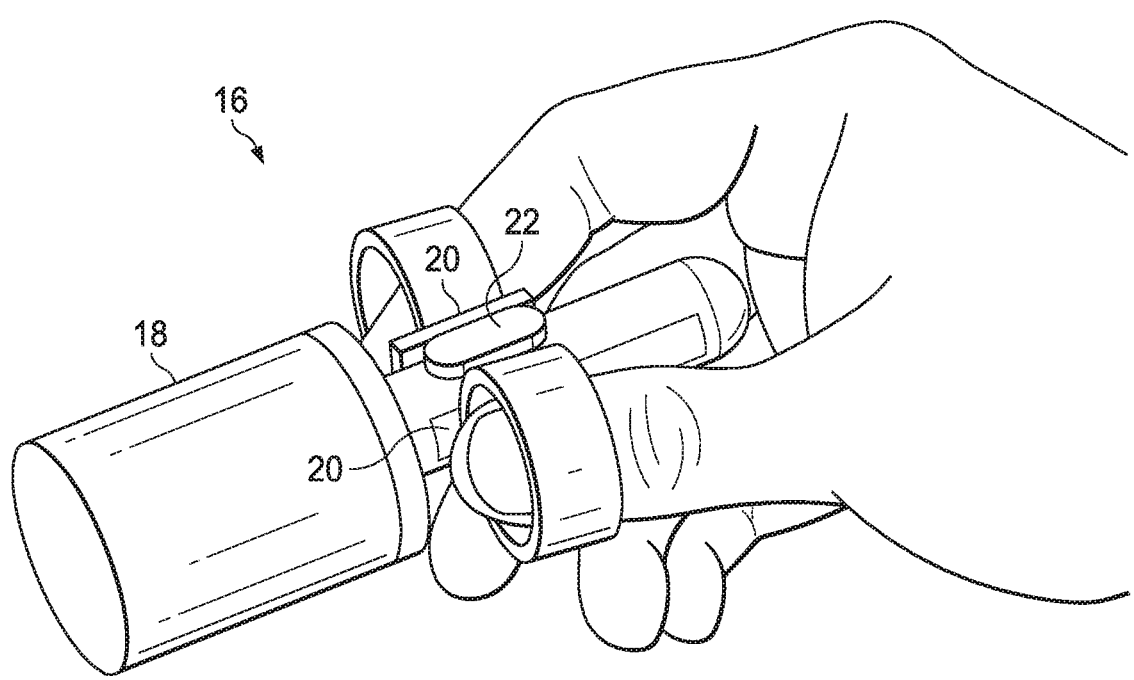
FIG. 2 illustrates an operator controller according to an embodiment of the present disclosure.

In this embodiment, the operator input system 16 includes one or a set of operator hand controllers 18 (FIG. 2) for controlling one or multiple medical instrument systems 14 or the endoscopic imaging system 15. The input system also, optionally, includes a pedal control device 24. The operator hand controllers 18 and the pedal control device 24 may be located at the side of the patient P. In various alternatives the operator hand controllers 18 may be tethered by power and/or signal transmission cabling or may be untethered/wireless. In other alternative embodiments, the operator hand controllers 18 may be located at an operator's console such as a surgeon's console, which may be located in the same room as operating table O. As shown in FIG. 2, the operator hand controllers 18 may include one or more of any number of a variety of input devices such as grip inputs 20 and trigger switches 22. The input devices may be used to, for example, close grasping jaw end effectors, apply an electrical potential to an electrode, deliver a medicinal treatment, or the like. In various alternatives, the operator input system 16 may additionally or alternatively include joystick devices, trackballs, data gloves, trigger-guns, hand-operated controllers, voice recognition devices, touch screens, body motion or presence sensors, and the like. In some embodiments, the operator hand controllers 18 will be provided with the same degrees of freedom as the medical instruments of the teleoperational assembly to provide the surgeon or other operator with telepresence, the perception that the control device(s) are integral with the instruments so that the surgeon or other operator S has a strong sense of directly controlling instruments as if present at the surgical site. In other embodiments, the operator hand controllers 18 may have more or fewer degrees of freedom than the associated medical instruments and still provide the surgeon or other operator with telepresence. Although hand controller 18 has been described here for a medical system, hand controller 18, or other input devices similar to hand controller 18, can be used in non-medical systems as well.

The teleoperational assembly 13 supports and manipulates the medical instrument system 14 while the surgeon or other operator S conducts the procedure from the patient side or another location within the surgical environment. An image of the surgical site within the patient can be obtained by the endoscopic imaging system 15, such as a stereo endoscopic imaging system, which can be manipulated by the teleoperational assembly 13 to orient the endoscopic imaging system 15. The number of medical instrument systems 14 used at one time will generally depend on the diagnostic or surgical procedure and the space constraints within the operating room among other factors. Each arm of the teleoperational assembly 13 may include a kinematic structure of one or more servo or non-servo controlled links. The teleoperational assembly 13 includes a plurality of motors that drive inputs on the medical instrument system 14. These motors move in response to commands from the control system 28. The motors include drive systems, which when coupled to the medical instrument system 14 may advance the medical instrument system 14 into a naturally or surgically created anatomical orifice. Other motorized drive systems may move the distal end of the medical instrument system 14 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the medical instrument system 14 for grasping tissue in the jaws of a biopsy device or the like. Medical instrument systems 14 may include end effectors having a single working member such as a scalpel, a blunt blade, a needle, an imaging sensor, an optical fiber, an electrode, etc. Other end effectors may include multiple working members, and examples include forceps, graspers, scissors, clip appliers, staplers, bipolar electro-cautery instruments, etc.

The control system 28 includes at least one memory and at least one processor, and typically a plurality of processors, for effecting control between the medical instrument system 14, the endoscopic imaging system 15, the operator input system 16, the display system 26, and other auxiliary systems which may include, for example, hand-held medical instrument systems, additional imaging systems, audio systems, fluid delivery systems, display systems, illumination systems, steering control systems, irrigation systems, and/or suction systems. The control system 28 also includes programmed instructions (e.g., a computer-readable medium storing the instructions) to implement some or all of the methods described in accordance with aspects disclosed herein. While the control system 28 is shown as a single block in the simplified schematic of FIG. 1, the control system 28 may include two or more data processing circuits with one portion of the processing optionally being performed on or adjacent the teleoperational assembly 13, another portion of the processing being performed at the operator input system 16, and the like. In various embodiments, the control system 28 may be housed in an electronics cart 30 to which the display system 26 or other peripheral equipment is mounted. The control system 28 may employ any of a wide variety of centralized or distributed data processing architectures. Similarly, the programmed instructions may be implemented as a number of separate programs or subroutines, or they may be integrated into a number of other aspects of the teleoperational medical systems described herein. In one embodiment, the control system 28 supports wireless communication protocols such as Bluetooth, IrDA, HomeRF, IEEE 802.11, DECT, and Wireless Telemetry.

In some embodiments, the control system 28 may include one or more controllers that receive force and/or torque feedback from the medical instrument system 14. Responsive to the feedback, the controllers transmit signals to the operator input system 16. The controller(s) may also transmit signals instructing teleoperational assembly 13 to move the medical instrument system(s) 14 and/or endoscopic imaging system 15 which extend into an internal surgical site within the patient body via openings in the body. Any suitable conventional or specialized controller may be used. A controller may be separate from, or integrated with, the teleoperational assembly 13. In some embodiments, the controller and teleoperational assembly 13 are provided as part of a teleoperational arm positioned adjacent to the patient's body.

The control system 28 can be coupled with the endoscopic imaging system 15 and can include a processor to process captured images for subsequent display, such as to a surgeon or some other personnel on the display system 26, on the surgeon's console, or on another suitable display located locally and/or remotely. For example, where a stereo endoscopic imaging system is used, the control system 28 can process the captured images to present the surgeon or some other personnel with coordinated stereo images of the surgical site. Such coordination can include alignment between the opposing images and can include adjusting the stereo working distance of the stereoscopic endoscope.

In alternative embodiments, the teleoperational medical system 12 may include more than one teleoperational assembly 13 and/or more than one operator input system 16. The exact number of teleoperational assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 3:
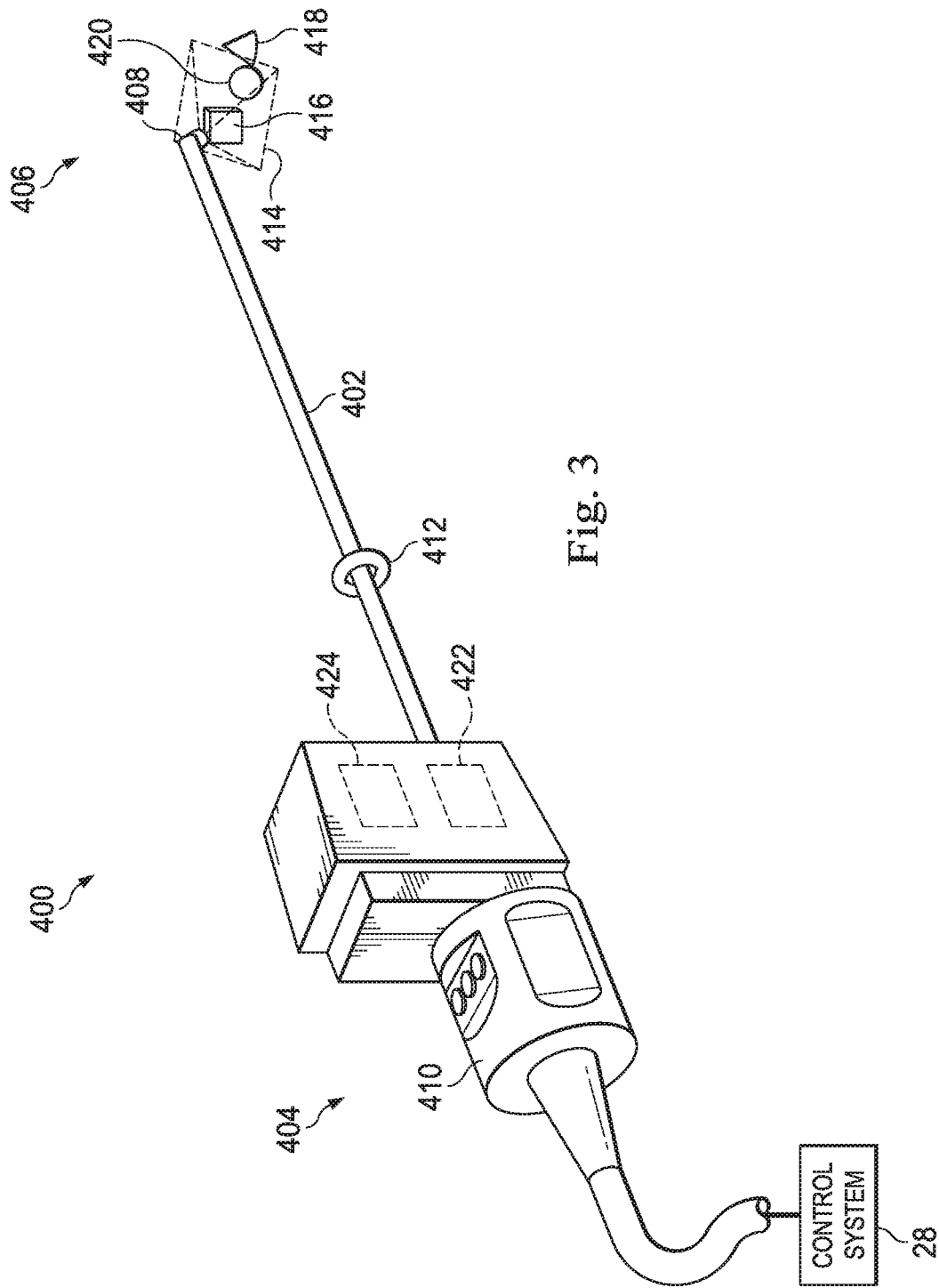
FIG. 3 illustrates a tool with an articulatable distal portion according to an embodiment of the present disclosure.

Referring to FIG. 3, illustrated is a tool with an articulable distal portion. In the particular example shown, the tool is a medical tool, and so is referred to as medical tool 400 in this application. However, as noted above, these techniques also apply to a variety of non-medical uses. For example, the tool shown in FIG. 3 may be a non-medical tool with an articulatable distal portion, such as an industrial tool, and entertainment tool, a teaching tool, or some other a non-medical tool. In some embodiments, the medical tool 400 is a hand-held device. In some embodiments, the medical tool 400 is designed to be mounted to a fixture that can be adjusted manually or with input devices located on or adjacent to the fixture. In some embodiments, the medical tool 400 is operably coupled to a teleoperational manipulator of a teleoperational medical system (e.g., a teleoperational medical system 12 of FIG. 1, or a teleoperational medical system where a surgeon or other operator controls the teleoperational manipulator using a console such as a surgeon's console).

As illustrated in FIG. 3, the medical tool 400 includes an elongate shaft 402 having a proximal end 404 and a distal end 406. An articulatable distal portion 408 is disposed at the distal end 406 of the shaft 402. A proximal housing 410 is disposed at the proximal end 404 of the shaft 402. The medical tool 400 also includes an actuation assembly 424 for driving motion of the articulatable distal portion 408. A sensor system 422 may be used for sensing the motion of the shaft 402. In some embodiments, the sensor system 422 is included in the medical tool 400. For example, the sensor system 422 and actuation assembly 424 may be disposed in the proximal housing 410. For a further example, as illustrated in FIG. 3, the sensor system 422 and actuation assembly 424 may be disposed on the shaft 402 next to the proximal housing 410. Alternatively, in some embodiments, the sensor system 422 is not included in the medical tool 400. In various embodiments, the sensor system 422, the actuation assembly 424, and the proximal housing 410 are in communication with a control system (e.g., the control system 28 of FIG. 1).

In some embodiments, the medical tool 400 is a hand-held device, and an operator may use his or her hands to move the proximal housing 410 to control the movement of the shaft 402 in one or more degrees of freedom relative to the proximal housing 410.

In some embodiments, the medical tool 400 is operably coupled to a teleoperational manipulator of a teleoperational medical system (e.g., a teleoperational medical system 12 of FIG. 1, or a teleoperational medical system where a surgeon or other operator controls the teleoperational manipulator using a console such as a surgeon's console). The proximal housing 410 may be removably connectable to the teleoperational medical system for releasably mounting and interfacing the medical tool 400 to a teleoperational manipulator (e.g., a teleoperational manipulator included in the teleoperational assembly 13 of FIG. 1) of the teleoperational medical system. The proximal housing 410 may transmit drive signals and/or motion input from the teleoperational medical system so as to move the shaft 402 in at least one degree of freedom relative to the proximal housing 410.

In the illustrated example of FIG. 3, the shaft 402 passes through a fulcrum pivot point 412 (indicated by a ring 412 of FIG. 3) of the medical tool 400, and the articulatable distal portion 408 includes an imaging device directed toward features 416, 418, and 420. The ring represents the natural fulcrum pivot point co-located with the incision at patient's body wall. This fulcrum point is common to minimally invasive "key-hole" surgery and is the genesis of a number of challenges for controlling view point and viewing direction, since proximal-end movements of inserted hand-held instruments produce inverted distal-end movements of the instrument tips and imaging devices. The features 416, 418, and 420 may be natural features within the patient anatomy. The imaging device has a field of view 414. In the illustrated example of FIG. 3, the field of view 414 has a three-dimensional pyramidal frustum shape, and is referred to as a viewing frustum 414 in the discussion below. In some embodiments, the imaging device is a stereoscopic imaging instrument with two imaging devices, and the viewing frustum 414 of the imaging device is the combined volume of the three-dimensional pyramidal frustums for each imaging device of the imaging device. In alternative embodiments, the field of view for the imaging device may provide another region of visualization, such as by providing a conical frustum shape, a slice-of-pie shape, or some other shape.

Figure 4A:
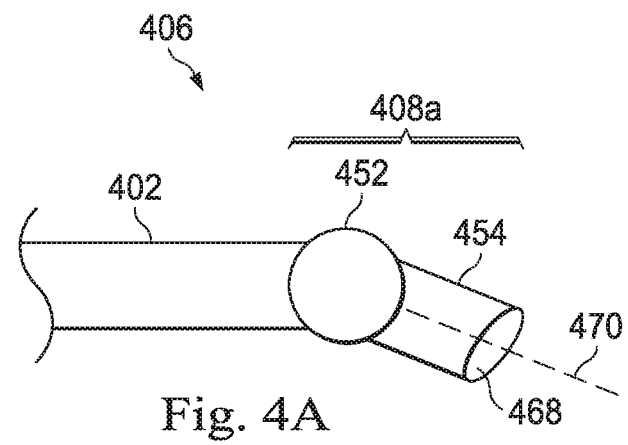
FIGS. 4A and 4B illustrate various embodiments of an articulatable distal portion of a tool according to the present disclosure.
Figure 4B:
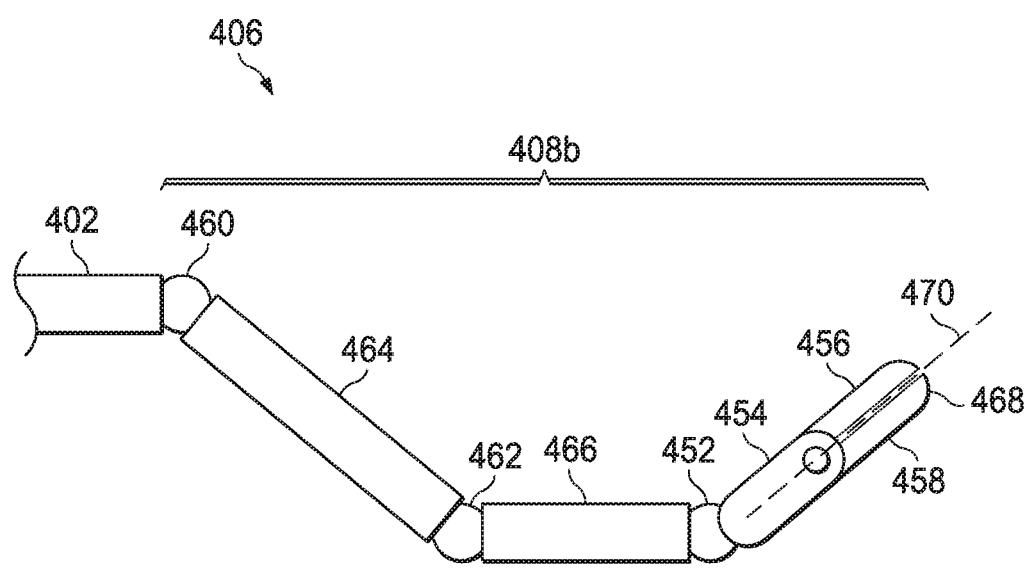

FIGS. 4A and 4B illustrate examples of the articulatable distal portion 408. Referring to FIG. 4A, the articulatable distal portion 408 may be a portion 408a including a device 454 coupled to a wrist assembly 452 driven by the actuation assembly 424. The wrist assembly 452 has pitch and yaw angular movement capabilities so that a distal tip 468 of the device 454 may be oriented up or down and to the right or left, and a combination thereof. A direction 470 from the wrist assembly 452 to the tip 468 may be referred to as a distal direction 470 of the articulatable distal portion 408a. The distal pitch/yaw angles of the wrist assembly 452 may be coordinated with roll of the shaft 402 to control the orientation of the device 454. In examples where the device 454 is an imaging device, for a distal direction 470, the shaft 402 may roll about that distal direction 470 to adjust the orientation of an imaging plane of the imaging device 454. In some embodiments, the device 454 is an imaging device including, for example, an optical imager, an ultrasonic imager, an electromagnetic imager such as a fluoroscopic imager, a thermal imager, a thermoacoustic imager, and any other suitable imagers. Alternatively, in some embodiments, the device 454 is an end effector, including for example an end effector having a single working member such as a scalpel, a blunt blade, an optical fiber, or an electrode. Other end effectors may include, for example, forceps, graspers, scissors, or clip appliers.

Referring to FIG. 4B, in some embodiments, the articulatable distal portion 408 includes a portion 408b including a wrist assembly 452 and a device 454, where the device 454 is an end effector with jaws 456 and 458. The distal direction 470 may be defined as a direction from the wrist assembly 452 to a distal tip 468 when the jaws 456 and 458 are closed. The articulatable distal portion 408 further includes joint assemblies (also called "joints") 460 and 462 and links 464 and 466. The wrist assembly 452 is coupled to the link 466. The joint assembly 460 couples the shaft 402 and the link 464, and the joint assembly 462 couples the link 464 and 466, so that the link 464 may pivot about the joint assembly 460 in pitch and yaw while the shaft 402 and link 466 remain parallel to each other. The joints 460 and 462 may cooperatively operate together so that as the link 464 pivots about the joint 460 in pitch and/or yaw, the link 466 pivots about the joint 462 in a complementary fashion so that the shaft 402 and the link 466 always remain parallel to each other. The joint assemblies 460 and 462 may provide a small amount of translation control to the articulatable distal portion 408. In some embodiments, the joint assemblies 460 and 462 are driven by the actuation assembly 424, and may be used to provide mechanical translational stabilization to the device 454 by the control system 28.

During a surgical minimally invasive teleoperational procedure, the surgeon (or other operator) S may view the surgical site within the patient's body on the display system 26 via images captured by the endoscopic imaging system 15 and/or other imaging systems. The imaging systems pose various challenges that may prevent the surgeon S and assistants A from achieving a natural and optimized viewing experience. For example, a hand-held imaging system operated by an assistant (or other personnel) A may be used to provide images of the surgical site to a surgeon. As discussed in detail below with respect to FIGS. 14A and 14B, conventionally, to provide images aligned with the perspective of the surgeon S, the assistant A may occupy the workspace of the surgeon S (e.g., by placing hands under the surgeon S's the arms or around the torso of the surgeon S) to direct the hand-held imaging system to the surgical site in a direction from the surgeon S. This sharing of a common workspace may be inconvenient and uncomfortable, and increasing the possibility of collision between the hand-held imaging system and the surgeon or between the hand-held imaging system and other tools. Further, in such an example, verbal communication between the surgeon S and assistant A is needed when the surgeon S requests to change the view.

Another challenge is that the motion of the proximal end of the imaging system may cause disruption, unsteadiness, and disorientation to the view provided by the imaging system. The proximal end of the imaging system may move for a variety of reasons. For example, the proximal end of the imaging system may be moved laterally (e.g., side-to-side) to avoid external collisions with the surgeon (or other operator) S's other medical instruments. The proximal end may be rolled (e.g., in the assistant (or other personnel) A's hand) for ergonomic reasons. The proximal end may be jostled due to unintentional movement of the assistant A. In some examples, the proximal end may be moved (e.g., retracted, pivoted, inserted) so that the surgeon S may observe a region or an object from various distances and directions. Such proximal end movements may require a skilled assistant A to perform the manipulations in a well-coordinated manner. Even so, the experience of transitioning between different view directions (e.g., looking up, looking down, or looking from/to the sides) may be disorienting and disruptive. Some surgeons forgo the benefits of enhanced depth perception afforded by a stereo endoscopic imaging system because of the unsteadiness of the view and the difficulty in maintaining the orientation associated with such a stereo endoscopic imaging system. Yet another challenge is that it is difficult for the surgeon to see around corners of the surgical site in the patient using those imaging systems.

Figure 5:
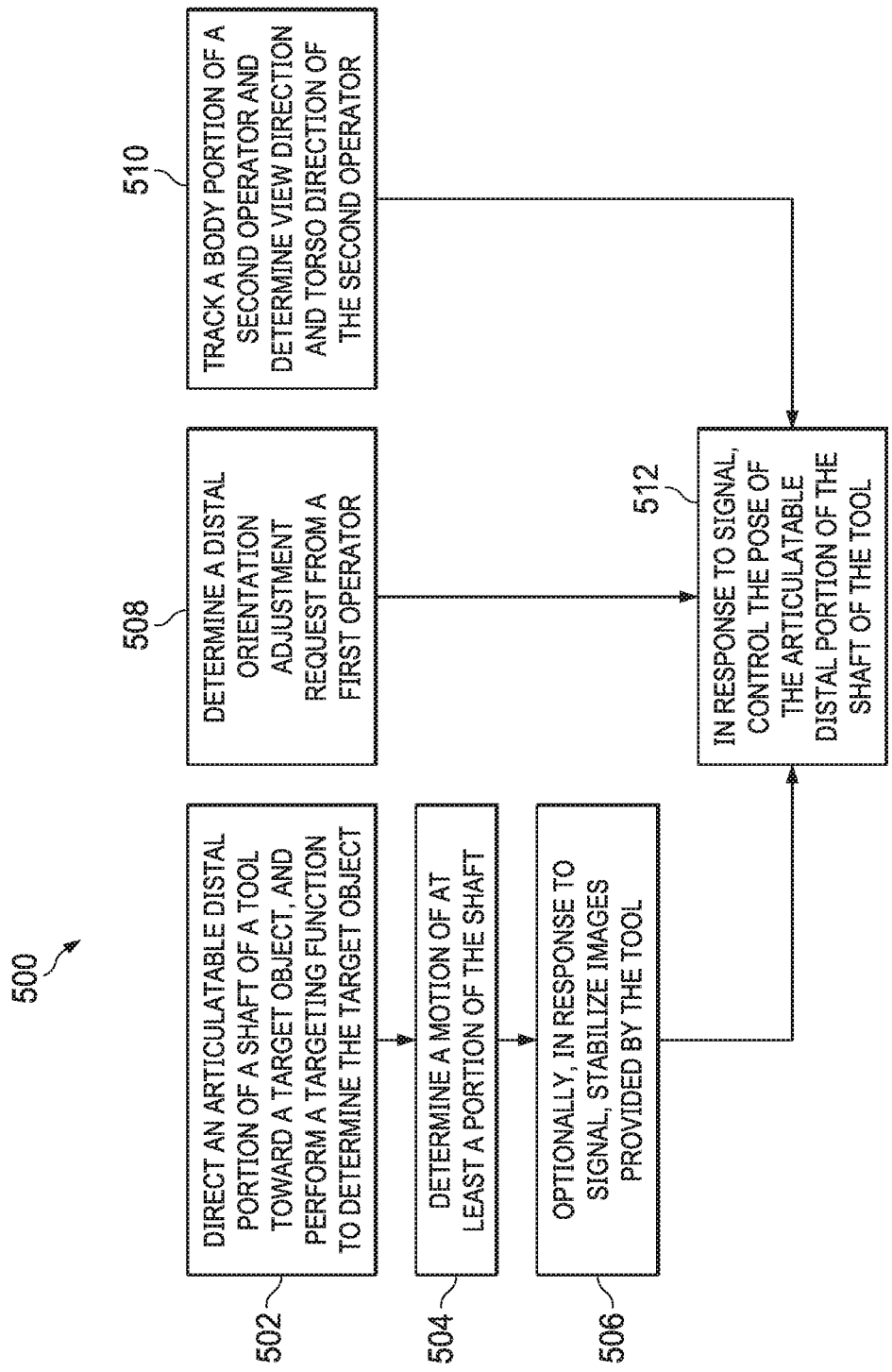
FIG. 5 is a flowchart providing a method for controlling a tool with an articulatable distal portion according to an embodiment of the present disclosure.

FIG. 5 illustrates a method 500 for controlling a tool (e.g., a medical tool 400) with an articulatable distal portion that addresses those challenges. Method 500 is discussed in portions of this application in connection with the medical tool 400. However, the technique illustrated by method 500 may also be used in connection with other medical tools or with non-medical tools. The method 500 is illustrated in FIG. 5 as a set of operations or processes 502 through 512. Not all of the illustrated processes 502 through 512 may be performed in all embodiments of method 500. Additionally, one or more processes that are not expressly illustrated in FIG. 5 may be included before, after, in between, or as part of the processes 502 through 512. In some embodiments, one or more of the processes may be implemented, at least in part, in the form of executable code stored on non-transitory, tangible, machine-readable media that when run by one or more processors (e.g., the processors of control system) may cause the one or more processors to perform one or more of the processes.

As shown in the method 500, the medical tool 400 may perform in different modes including, for example, a target tracking mode as provided by processes 502, 504, 506, and 512, a manual control mode as provided by processes 508 and 512, and an operator-steered mode as provided by processes 510 and 512. More than one mode (e.g., the target tracking mode and the operator-steered mode) may be enabled in a medical tool 400 at the same time.

In various embodiments, the operator may use an operator input system 16 (e.g., by pressing a particular button) to enable or disable a particular mode. For example, an operator may use the operator input system 16 to disable the target tracking mode. In such an example, the control system 28 does not control the pose of the articulatable distal portion 408 for maintaining the orientation of the articulatable distal portion 408 directed toward a target (e.g. target tissue, other target object, or other target region) in response to the shaft movement. By controlling the articulable distal portion of the scope, various advantages of various embodiments may be achieved. One advantage of some embodiments is that the articulable disable portion may remain directed towards the target. Another advantage of some embodiments is that one or more targets are kept within the field of view. Yet another advantage of some embodiments is that a distal roll orientation of the imaging device in the world may be preserved. Yet another advantage of some embodiments is that transient disturbances in position or orientation of the imaging device are rejected.

Referring to processes 502, 504, 506, and 512, when operating in the target tracking mode, as the proximal housing 410 of the medical tool 400 is moved, the control system 28 controls the articulatable distal portion 408 so that the articulatable distal portion 408 remains directed toward a target. In an example, by continuously monitoring the motion of the proximal housing 410 and controlling the orientation and/or position of the articulatable distal portion 408 accordingly, this operation provides a stable, continuous, and correctly oriented pointing at a target (e.g. target tissue, other target object, or other target region) from different distances and directions. As a specific example, where the articulatable distal portion 408 includes an imager, this technique provides a stabilized, continuous, and correctly oriented view for imaging a viewing target from different distances and directions.

At process 502, the control system 28 determines a target (e.g. target tissue, a target object, a target region, etc.) in the patient anatomy for the medical tool 400. In some embodiment, the medical tool 400 includes an imaging device, and the target may be selected based on images captured by that imaging device of the medical tool 400. Alternatively, in some embodiment, the medical tool 400 does not include an imaging device, and the target may be selected based on images captured by another medical tool.

During the process 502, an operator may perform a targeting function to determine a target in the surgical site. The proximal housing 410 may be moved (e.g., by an operator's hand or by a teleoperational manipulator) to control the movement of the shaft 402 and thereby the view captured by the imaging device and provided to the operator.

Referring to FIGS. 6A and 6B, in some embodiments, the device 454 of the articulatable distal portion 408 of a tool (e.g. the medical tool 400) is an imaging device, and the operator may select a target within a viewing frame of the imaging device and from an image data set captured by that imaging device. FIGS. 6A-6C are discussed in portions of this application in connection with the medical tool 400. However, the technique illustrated by these figures may also be used in connection with other medical tools or with non-medical tools.

FIG. 6A illustrates a view 602 in the patient anatomy provided by the imaging device included in the articulatable distal portion 408 and displayed on the display system 26. The view 602 includes features 416, 418, and 420, where the feature 420 is located in a center area 604 of the view 602. The operator may perform a targeting function (e.g., by pressing a button on the operator input system 16 of FIG. 1) when the feature 420 appears at the center area 604 of the view 602, thereby selecting the feature 420 as the target. Referring to FIG. 6B, in some examples, the operator may select a feature that is not located in a center area of the view as the target. Illustrated in FIG. 6B is a view 606 in the patient anatomy captured by the imaging device included in the articulatable distal portion 408 and displayed on the display system 26. The view 606 includes features 416, 418, and 420. In the illustrated example of FIG. 6B, the operator draws a target area 608 (e.g., by using an operator input system 16) and submits the target area 608 for the targeting function. The control system 28 may then determine the feature 420 as the target (which may then be referred to as target 420) based on the target area 608.

Referring to FIG. 6C, in some embodiments, the articulatable distal portion 408 of the medical tool 400 may not include an imaging device. In such embodiments, the operator may select a target based on a view provided by another medical tool (e.g., the endoscopic imaging system 15 of FIG. 1, a real-time fluoroscopic image provided by a fluoroscopic imager, a real-time image provided by an ultrasonic imager, etc.). FIG. 6C provides a view 610 in the patient anatomy captured by an imaging device (e.g., the endoscopic imaging system 15) and displayed on, for example, the display system 26. The view 610 includes features 416, 418, and 420, the distal end 406 of the medical tool 400, and the articulatable distal portion 408a coupled to the distal end 406. Based on the view 610, the operator may determine that the device 454 is directed toward the feature 420 (e.g., the feature 420 is along the distal direction 470 of the articulatable distal portion 408a). The operator may then perform a targeting function (e.g., using an operator input system 16), which selects the feature 420 as the target.

In some embodiments, the targeting function may be performed to select a target orientation of the device 454 with respect to a feature (e.g., a tumor, a vessel, etc.) in the patient's anatomy. In such embodiments, the control system 28 may control the articulatable distal portion 408 in response to the proximal end movement so that the device 454 maintains that target orientation with respect to the feature.

In various embodiments, the targeting function may be performed with a stereo endoscopic imaging device or a monoscopic endoscopic imaging device. In an example where a stereo endoscopic imaging device is used, the control system 28 may determine a three-dimensional (3D) location of the target by using stereo correlation with a calibrated camera model. In some embodiments, the control system 28 may process the images provided by the imaging device (e.g., using a scale-invariant feature transform (SIFT) algorithm) to detect local features (e.g., features 416, 418, 420) in the images. Such local features may be tracked in a continuous manner from frame to frame. Additionally, the use of the local features in the images may enable the medical tool 400 to track, in the view, tissues and organs as they are manipulated (e.g., by a medical instrument system operated by the surgeon or some other operator).

Referring back to FIG. 5, the method 500 may proceed to a process 504, where the control system 28 determines a motion of the shaft 402 of the medical tool 400. In some embodiments, the control system 28 may determine the motion of the shaft 402 based on information provided by the sensor system 422. The sensor system 422 may include one or more sensors including, for example, an inertial measurement unit (IMU), an electromagnetic sensor, an optical tracking system, an image tracking system, a hybrid sensor system, other suitable sensor systems, and a combination thereof. In some embodiment, the medical tool 400 is coupled to a teleoperational manipulator of a teleoperational medical system. In such embodiments, the sensor system may include encoders of the teleoperational manipulator coupled to the medical tool 400.

In various embodiments, different types of sensors of the sensor system 422 may be disposed at different locations with respect to the shaft 402 and the target 420. Referring to FIG. 3, in an example, an IMU is located at the proximal end 404 of the shaft 402. The IMU is configured to track the motion (e.g., linear movements, angular movements) of the proximal housing 410 of the shaft 402 with respect to the target 420.

In another example, the sensor system 422 includes an image tracking system, where the image tracking system includes a device 454 of the articulatable distal portion 408 and the device 454 is an imaging device. The control system 28 may receive a plurality of images from the image tracking system, and perform feature extraction and analysis of the target in the plurality of images. In an example, a plurality of features (e.g., features 416, 418, and 420) are extracted from the images, and the analysis of the target in the plurality of images may track the target with respect to the other extracted features in the images.

In some embodiments, the image tracking system may provide information for the pose of the distal end 406 with respect to the target, which may be used by the control system 28 to control the pose of the articulatable distal portion 408 within the surgical coordinate space with respect to the target. In such embodiments, the control system 28 may control the articulatable distal portion 408 so that it remains directed toward the target, where the shaft 402 may be a rigid shaft, a substantially rigid shaft, or a flexible shaft.

In some embodiments, the control system 28 determines the motion of the shaft 402 without using the sensor system. In such embodiments, the medical tool 400 is coupled to a teleoperational manipulator of a teleoperational medical system, where the teleoperational manipulator is configured for control of shaft motion. The control system 28 may determine the motion of the shaft 402 based on one or more commands issued for driving the teleoperational manipulator. Alternatively, in some embodiments, the control system 28 determines the motion of the shaft 402 based on both the sensor system and the one or more commands issued for driving the teleoperational manipulator coupled to the medical tool 400.

Referring back to FIG. 5, optionally, the method 500 may proceed to a process 506. At process 506, the control system 28 may use the information provided by the sensor system 422 to stabilize the image captured by the medical tool 400 by digital image stabilization, mechanical image stabilization, or a combination thereof. In some examples, the medical tool 400 is a stereo endoscopic imaging system. In such an example, the control system 28 may perform mechanical image stabilization by controlling the pose of the articulatable distal portion 408. In an example, the control system 28 may control the joint assemblies 460 and 462 of FIG. 4B to provide translational mechanical stabilization. In an example, the control system 28 may control the wrist assembly 452 of FIGS. 4A and 4B to provide rotational mechanical stabilization.

In some examples, the medical tool 400 is a monoscopic endoscopic imaging system. In such an example, in addition to the mechanical image stabilization substantially similar to that performed on the stereo endoscopic imaging system discussed above, the control system 28 may perform digital image stabilization based on information provided by the sensor system 422. In an example, the IMU is sensitive to vibration, and the control system 28 may perform digital image stabilization based on the sensing information provided by the IMU.

Referring back to FIG. 5, the method 500 may proceed to a process 512, where in response to a signal including the motion information of the shaft 402, the control system 28 controls the pose of the articulatable distal portion 408 so that the articulatable distal portion 408 remains directed toward the target 420. In some examples, the articulatable distal portion 408 remains directed toward the target 420 where the target remains along a viewing direction associated with an orientation 802 of the viewing frustum 414. In some examples, the articulatable distal portion 408 remains directed toward the target 420 where the viewing frustum 414 remains to enclose the target 420 or a center of the target 420. In such examples, the target 420 may not be always at a center area of the view. In some examples, the articulatable distal portion 408 remains directed toward the target 420 where the target remains to be along the distal direction 470 of the articulatable distal portion 408.

FIG. 7 illustrates an example of a tool (e.g. the medical tool 400) operating in the target tracking mode in response to a proximal end movement 700 moving through positions 702-1, 702-2, 702-3, and 702-4. The positions 702-1 and 702-4 are the starting position and the ending position of the proximal end respectively, and positions 702-2 and 702-3 are two intermediate positions of the proximal end. The control system 28 continuously monitors the motion of the shaft 402. In response to the determination of the motion of the shaft 402, the control system 28 continuously controls the articulatable distal portion 408 so that the articulatable distal portion 408 remains directed toward the target 420. The control system 28 may send commands to the actuation assembly 424, which drives motion of the articulatable distal portion 408 (e.g., by driving the wrist assembly 452 of FIGS. 4A and 4B, the joint assemblies 460 and 462 of FIG. 4B) according to those commands.

The example of FIG. 7 illustrates such continuous monitoring and control by the control system 28. The proximal end of the medical tool 400 starts at the position 702-1, where the articulatable distal portion 408a has a viewing frustum 414-1 directed toward the target 420. The proximal end of the medical tool 400 then moves to the position 702-2. The control system 28 determines the motion of the shaft 402 caused by such movement (e.g., based on the sensor system 422, commands issued for driving the teleoperational manipulator coupled to the medical tool 400, or a combination thereof), and uses the actuation assembly 424 to drive motion (e.g., pitch and/or yaw) of the articulatable distal portion 408, so that the articulatable distal portion 408 has a viewing frustum 414-2 directed toward the target 420. Similarly, after determining that the proximal end of the medical tool 400 moves to the position 702-3, the articulatable distal portion 408 is controlled so that it has a viewing frustum 414-3 directed toward the target 420. In like manner, after determining that the proximal end of the medical tool 400 moves to the position 702-4, the articulatable distal portion 408 is controlled so that it has a viewing frustum 414-4 directed toward the target 420. In some embodiments, the target 420 is at the center of each of the viewing frustums 414-1, 414-2, 414-3, and 414-4. As shown in FIG. 7, during the proximal end movement 700, the viewing frustum of the articulatable distal portion 408 remains directed toward the target 420.

In an example where the sensor system 422 includes an image tracking system, the control system 28 include a visual controller that receives the image feedback from the imaging device of the articulatable distal portion 408 of the medical tool 400, and performs image-based visual servoing to control the motion of the articulatable distal portion 408. Any other suitable conventional or specialized controller may be used.

In various embodiments, the distal degrees of freedom of the articulatable distal portion 408 are controlled to keep the articulatable distal portion 408 directed toward the target 420 while preserving the roll orientation of the view with respect to a predetermined reference plane. As such, the view provided by the medical tool 400 maintains to be level with the reference plane. In some embodiments, the reference plane is a horizontal plane or is determined based on a table top of an operating table O in the surgical environment. Alternatively, in some embodiments, the reference plane is determined based on an input from an operator (e.g., using an operator input system 16). For example, the operator may perform a reference plane selection function (e.g., using the operator input system 16) based on a particular image displayed on the display system 26, where that particular image is level with the desired reference plane. In that example, the control system 28 may determine the reference plane based on that particular image. In another example, the operator may perform a targeting function to select a target based on a particular image displayed on the display system 26, and the control system 28 may determine the reference plane based on that particular image used for selecting the target.

In some embodiments, providing the target tracking mode and views maintained to be level allows the assistant (or some other personnel) A to operate a hand-held medical tool 400 at a location (e.g., facing the surgeon (or some other personnel) S across the operational table O) outside of the workspace of the surgeon S. However, in those embodiments, the shaft 402 and the articulatable distal portion 408 may approach the patient anatomy from a direction (also referred to as an approaching direction of the medical tool 400) opposite to a working direction of the surgeon. In some examples, the working direction of the surgeon aligns with an orientation of the surgeon's torso with respect to the surgical site (e.g., in a surgical environment that the surgeon is located at the side of the patient P). In some examples, the working direction of the surgeon aligns with an orientation of the surgeon's head and/or eyes with respect to the display system (e.g., in a surgical environment that the surgeon wears a head-mounted display system displaying a view of the surgical site). The medical tool 400 may be controlled (e.g., by the control system 28 and/or by the assistant A) to ensure the images are upright (instead of top-bottom inverted), leveled, and have a left-to-right order consistent with that from the perspective of the surgeon, even when the shaft 402 and the articulatable distal portion 408 approach the patient anatomy from a direction different from a working direction of the surgeon. In an example, an assistant A (e.g., assistant A1 of FIG. 12) is standing facing the surgeon S, and the shaft 402 and the articulatable distal portion 408 approach the patient anatomy from a direction opposite from a working direction of the surgeon. In that example, the medical tool 400 is controlled (e.g., by the control system 28 or by the assistant A) to ensure that in the image provided by the medical tool 400, the left-to-right order of the features is consistent with (instead of left-right inverted) the perspective of the surgeon S. In an example, such a view including upright, leveled, and not left-right inverted features may be achieved by controlling (e.g., retracting, inserting, rolling, pivoting) the proximal housing 410. In some examples, such a view may be achieved by aligning the viewing direction associated with the orientation 802 with the working direction of the surgeon by the control system 28, which will be discussed in detail below with respect to FIG. 12.

In some embodiments, the medical tool 400 is controlled (e.g., by controlling the view direction associated with the orientation 802 using the control system 28) based on various reference planes (e.g., a level reference plane) and reference directions (e.g., an upright reference direction, a left-to-right reference direction), so that the images captured by the image device of the medical tool 400 are leveled, upright, and have a desired left-to-right order regardless of the approaching direction of the medical tool 400. For example, the medical tool 400 is controlled so that the images are level with a level reference plane (e.g., a horizontal plane, a table top of an operating table O in the surgical environment, a plane selected by the operator). For a further example, the medical tool 400 is controlled so that the images are upright (e.g., top-to-bottom aligned) with respect to an upright reference direction (e.g., a direction perpendicular to the level reference plane, a direction selected by an operator). For a further example, the medical tool 400 is controlled so that the left-to-right order of the images is aligned with a left-to-right reference direction (e.g., a direction parallel to the level reference plane, a direction selected by the operator). In some embodiments, the reference planes and directions are determined based on the working direction of the surgeon (or some other personnel) S. Alternatively, in some embodiments, the reference planes and directions are determined based on an input from an operator (e.g., using an operator input system 16). For example, the operator may perform a reference selection function (e.g., using the operator input system 16) when a particular image is displayed on the display system 26. The control system 28 may then determine the reference planes and directions based on that particular image.

Referring to FIG. 8A, illustrated is the tool (e.g. medical tool 400) arranged in the position 702-1. As discussed above, the articulatable distal portion 408 is controlled so that the viewing frustum 414-1 has an orientation 802 directed toward the target 420. In some examples, the viewing direction associated with the orientation 802 may be the same as the distal direction 470. Illustrated in FIG. 8B is an image 804 of the viewing frustum 414-1, which may be displayed on the display system 26 of FIG. 1. As shown in FIG. 8B, the target 420 is in a center area 604 of the image 804 and is level with the ground of the surgical environment. Further, in the image 804, the target 420 and its neighboring features 416 and 418 appear upright. In an implementation of the example of FIGS. 8A and 8B, the operator is a surgeon and is located at the proximal end 404 of the shaft 402, and the left-to-right order of the features in the image of 8B is the same as the features with respect to the operator's working direction. Alternatively, in examples where the operator is an assistant operating the medical tool 400 for a surgeon, the proximal housing 410 is adjusted and the pose of the articulatable distal portion 408 is changed so that the left-to-right order of the features in the image of 8B is displayed from the perspective of the surgeon's working direction.

Referring to FIGS. 9A and 9B, after the proximal housing 410 of the shaft 402 moves to the position 702-4, the articulatable distal portion 408 is controlled so that the viewing frustum 414-4 has an orientation 802 directed toward the target 420. Illustrated in FIG. 9B is an image 902 of the viewing frustum 414-4, which may be displayed on the display system 26 of FIG. 1. As shown in FIG. 9B, the target 420 is in a center area 604 of the image 902, and is level with the ground of the surgical environment. Further, the target 420 and its neighboring features 416 and 418 remain upright in the image 902. In an implementation of the example of FIGS. 9A and 9B, the operator is a surgeon and is located at the proximal end 404 of the shaft 402, and the left-to-right order of the features in the image of 9B is aligned to the left-to-right order of the features with respect to the operator's working direction. Alternatively, in examples where the operator is an assistant operating the medical tool 400 for a surgeon, the proximal housing 410 is adjusted so that the left-to-right order of the features in the image of 9B is displayed from the perspective of the surgeon's working direction.

It is noted that while an articulatable distal portion 408 including an imaging device is used as an example in FIGS. 7, 8A, 8B, 9A, and 9B, the device 454 of the articulatable distal portion 408 may be an end effector or any other devices. In an example, in the target tracking mode, the control system 28 may control the articulatable distal portion 408 in response to the proximal end movement so that the end effector remains directed toward a target. In another example, the operator may provide the control system 28 a target orientation with respect to a feature in the patient's anatomy for the end effector. In such an example, the control system 28 may control the articulatable distal portion 408 in response to the proximal end movement so that the end effector maintains a target orientation with respect to the feature (e.g., perpendicular to a vessel).

It is also noted that, while FIGS. 7, 8A, 8B, 9A, and 9B are discussed in portions of this application in connection with a medical tool such as medical tool 400, the technique illustrated by these figures may also be used in connection with other medical tools or with non-medical tools.

Referring back to FIG. 5, as discussed above, at processes 508 and 512, the medical tool 400 may operate in a manual control mode. At process 508, the control system 28 determines whether an operator has performed a distal orientation adjustment request (e.g., by using an operator input system 16 located at the side of the patient P or at an operator console such as a surgeon's console). At process 512, in response a determination that the operator has performed the distal orientation adjustment request, the control system 28 controls the pose of the articulatable distal portion based on the distal orientation adjustment request. In the manual control mode, the control system 28 maintains the horizontal level of the images while the view direction (e.g., the orientation 802 of the viewing frustum 414) is manually changed by an operator (e.g., using an operator input system 16), and as such, the images during the transmission between different view directions remain upright.

In various embodiments, the control system 28 may receive a distal orientation adjustment request performed by the operator via the operator input system 16. The distal orientation adjustment request may include a steering input for the new view direction (e.g., providing a first distance in the left/right direction, and a second distance in the up/down direction compared to the current view direction). While the pitch/yaw degrees of freedom of the articulatable distal portion 408 may be changed according to the distal orientation adjustment request, the shaft 402 steers the tip roll, so that the target(s) always appear upright in the images. Such a change in the view direction requires coordinated motion of pitch, yaw, and roll degrees of freedom. The control system 28 maps the steering input in an image-centric manner using an image coordinate frame, and the result is then inversely mapped to the corresponding pitch/yaw joint movements of the articulatable distal portion 408. The control system 28 controls the pose of the articulatable distal portion 408 based on those pitch/yaw joint movements (e.g., by using the actuation assembly 424).

Referring to FIGS. 10A, 10B, 11A, and 11B, illustrated therein are the medical tool 400 before and after the view direction is changed under the manual control mode. It is worth noting that while FIGS. 10A, 10B, 11A, and 11B are discussed in portions of this application in connection with a medical tool such as medical tool 400, the technique illustrated by these figures may also be used in connection with other medical tools or with non-medical tools.

FIG. 10A is substantially similar to FIG. 9A other than the differences described herein. As shown in FIG. 10A, there are additional features 1002, 1004, and 1006 that are located next to the features 416, 420, and 418. FIG. 10B illustrates an image 1008 of the viewing frustum 414-4, which includes features 416, 418, and 420. After receiving a distal orientation adjustment request for changing the view direction from the target 420 to a position corresponding to the feature 1002, the control system 28 controls the pose of the articulatable distal portion 408.

Referring to FIG. 11A, illustrated is the medical tool 400 after the process 512 is performed in response to the distal orientation adjustment request. In the illustrated example of FIG. 11A, the proximal end of the shaft 402 remains at the position 702-4, while the articulated distal portion 408 has been controlled so that its viewing frustum 414-5 has an orientation 802 directed toward the feature 1002. FIG. 11B illustrates an image 1102 of the viewing frustum 414-5, and the features 1002, 1004, 1006 appear upright in the image 1102. By using such approach, the images during the transition between different view directions always remain upright in the world.

Referring back to FIG. 5, as discussed above, the medical tool 400 may operate under an operator-steered mode as provided by processes 510 and 512. Such an operator-steered mode provides a surgeon (or other operator) a hands-free way to control the view (e.g., by moving his or her torso, head, or eyes), and visually explore a larger space without interruption or the need for verbal communication with an assistant who is operating the medical tool 400.

At process 510, a tracking system is configured to track a working direction of a surgeon. In some examples, the tracking system is configured to track at least a portion of a surgeon's body including, for example, the surgeon's head, eye(s), and torso. In alternative embodiments, the tracking system is configured to track an insertion direction of a tool (e.g., a shaft direction of a laparoscopic instrument) operated by the surgeon. The tracking information captured by the tracking system may be used to determine a working direction (e.g., a view direction, a torso direction, a tool insertion direction) of the surgeon, which is used to control the articulatable distal portion 408 of the medical tool 400. In various embodiments, a tip of the articulatable distal portion 408 of the medical tool 400 may be controlled such that it is aligned with the working direction of the surgeon, which is particularly useful when a shaft 402 of the medical tool 400 has a different approach direction to the target compared to the tool operated by the surgeon.

Referring to FIG. 12, illustrated therein is a surgery-type medical environment 1200 substantially similar to the environment 10 of FIG. 1 except for the differences described below. In the surgical environment 1200, an assistant (or some other personnel) A1 opposing the surgeon (or some other personnel) S is holding the proximal housing 410 of a medical tool 400, where the medical tool 400 is an endoscopic imaging system. The display system 26 may present images of the surgical site captured by the medical tool 400. The assistant A1 may move the proximal housing 410 of the medical tool 400 to control the images captured by the medical tool 400. The assistant A1 may also be referred to as a primary operator of the medical tool 400.

In some embodiments, a tracking system 1202 is used to track at least a portion of a surgeon S's body, and the tracking information may be used in subsequent processes to control the articulatable distal portion 408 of the medical tool 400, thereby controlling the view captured by the medical tool 400 and displayed on the display system 26. By using such a tracking system 1202, the surgeon S may control the view captured by the medical tool 400 by moving his or her body. The surgeon S may be referred to as a secondary operator of the medical tool 400. By using the tracking system 1202, the medical tool 400 may be controlled by the primary operator A1 and the secondary operator S. In an embodiment, the primary operator A1 may perform coarse control of the view provided by the medical tool 400 by moving the proximal housing 410 of the medical tool 400, while the secondary operator S may perform fine control of the view provided by the medical tool 400 using the tracking system 1202.

In the example of FIG. 12, the environment 1200 includes a tracking system 1202 that detects objects or markers within a spatial volume 1204 of the environment 1200. In this embodiment, the tracking system 1202 may be an optical tracking system, but in various alternative embodiments, other tracking systems such as acoustic, electromagnetic, IMU, or hybrid tracking systems may be used. In some embodiments, an optical tracking system may have multiple uses beyond tracking the surgeon S's body. For example, the tracking system 1202 may also be used for tracking hand motion or for image registration. As another example, the tracking system 1202 may also be used for tracking motions of shafts of medical tools such as the medical tool 400. Shaft motion may be tracked indirectly, such as by tracking a proximal portion of the medical tool proximal to the shaft, and combining the tracking data for the proximal portion of the medical tool with other information relating the shaft to the proximal portion. Examples of such other information include as shape sensor or other sensor data, and kinematic information and models.

In the embodiment of FIG. 12, the tracking system 1202 is mounted to the display system 26 to track a spatial volume 1204 in front of the display. The tracking system 1202 may track markers within the spatial volume 1204 to determine the orientation of the surgeon S's body. In alternative embodiments, the tracking system may be mounted elsewhere in the surgical environment 1200 and may use a transformation between the display system position coordinates and the tracking system coordinates to determine the position and orientation of markers or objects relative to the display system 26. In alternative embodiments, the tracking system may include a head-mounted wearable device, a camera, or other sensor coupled to the surgeon's head (e.g., worn by the surgeon) which tracks the motion of the surgeon's head and/or eyes relative to static or movable markers with known positions in the surgical environment 1200. In alternative embodiments, the display system 26 may be a virtual display system that has a fixed or known virtual projection plane within the surgical environment 1200.

FIG. 12 illustrates the surgeon S wearing a set of optical markers 1206 that may be tracked by the tracking system 1202. In this embodiment, the markers 1206 are rigidly attached to the clothing worn by the surgeon S. In some embodiments, the markers tracked by the tracking system 1202 include natural markers corresponding to natural portions of the body of the surgeon S (e.g., pupils or glint points of the surgeon S's eyes, outer edges of the surgeon S's nose, outer edges of the surgeon S's mouth, the lowest point of the surgeon S's chin, etc.). In some embodiments, the markers tracked by the tracking system 1202 include markers rigidly attached to a face mask worn by the surgeon S, which may be used to track the head orientation of the surgeon S. In some embodiments, the markers include fiducial markers attached to glasses, such as passive polarized glasses used with stereoscopic displays. Other markers such as the outline of the surgeon S's face, head, and torso may also be tracked by the tracking system 1202.

Referring again to the method 500 of FIG. 5, at process 510, tracking of one or more markers (including natural landmarks or artificial markers) may be used to estimate the position and orientation of the surgeon (or some other operator) S's torso, head, face, eyes, gaze, or other body portion. The positions and orientations may be used to compute a working direction of the surgeon S. The working direction of the surgeon S may be, for example, computed based upon the torso orientation, head orientation, eye gaze direction, or a combination thereof.

The method 500 may proceed to process 512, during which the pose of the articulatable distal portion 408 of the medical tool 400 is controlled in response to the detected motion of the surgeon provided by the tracking system 1202.

In some embodiments, the control system 28 may determine a motion of the surgeon, which causes a change in the surgeon S's working direction (e.g., relative to a display system or a surgical site). The control system 28 then controls the pose of the articulatable distal portion 408 based on the detected motion of the surgeon. In an example, the pose of the articulatable distal portion 408 is controlled so that the orientation of the viewing frustum 414 is aligned with the working direction of the surgeon S.

In some embodiments, as the distal pitch/yaw joints of the wrist assembly 452 of the articulatable distal portion 408 approach a range of motion limits, the control system 28 provides an indication to the assistant A on the proximal housing 410 to move the proximal housing 410 of the medical tool 400 in the corresponding direction. In some embodiments, such indication to the assistant A may be provided using an arrangement of lights (e.g., light emitting diode (LED) lights) on the proximal housing 410. Alternatively, the proximal housing 410 may haptically render directional cues to the assistant A. The assistant A may then move the proximal end according to the indication.

Referring to FIG. 13, illustrated therein is an example of a control system 1400 (e.g., control system 28 for the example of FIG. 1, 3, 12 or a portion thereof). The control system 1400 may be used to control movement of the articulatable distal portion 408 of the medical tool 400, as commanded by movement (e.g., of a proximal end 404 of the medical tool 400) of an operator (e.g., assistant A). In some embodiments, the control system 1400 includes an actual joint state estimator 1402 for generating actual state estimates (e.g., pose, velocity) for the joints of the articulatable distal portion 408 (e.g., based on inputs from a sensor system 422). The control system 1400 further includes a desired joint state generator 1404 to generate the desired joint states for the joints of the articulatable distal portion 408 (e.g., based on a target provided by an operator). A joint controller 1406 of the control system 1400 may control the joints of the articulatable distal portion 408 based on the actual state estimates and the desired joint states of those joints. A proximal output unit 1408 may detect that joints of the articulatable distal portion 408 approach a range of motion limits, and provide an indication to an operator (e.g., on the proximal housing 410) to move the proximal housing 410 of the medical tool 400 in a particular direction.

As shown in FIG. 13, in some embodiments, the actual joint state estimator 1402 includes a forward kinematics and sensor fusion unit 1410 and a manipulator Jacobian unit 1412. The forward kinematics and sensor fusion unit 1410 may receive, from a sensor system (e.g., sensor system 422) of the medical tool 400, proximal end information (e.g., positions, orientations, velocities of the proximal end 404). The forward kinematics and sensor fusion unit 1410 may further receive, from the joint controller 1406, joint state information of the joints (e.g., joint 452 of FIG. 4A, joints 452, 460, and 462 of FIG. 4B) of the articulatable distal portion 408. The forward kinematics and sensor fusion unit 1410 may generate actual joint state estimates of the joints of the articulatable distal portion 408 based on the proximal end information and/or joint state information using forward kinematics and sensor fusion. In some examples, the actual joint state estimates of the joints of the articulatable distal portion 408 are determined based on the manipulator Jacobian between joint velocities and tip velocities provided by the manipulator Jacobian unit 1412.

In some embodiments, the desired joint state generator 1404 includes a transformation unit 1414 configured to receive target information for targets (e.g., target points, target orientation planes) selected by an operator, transform the received target information to a reference frame of the wrist assembly 452 of the articulatable distal portion 408, and provides transformed target information in the reference frame of the wrist assembly 452. A desired tip orientation unit 1416 determines a desired orientation of the distal tip 468 based on the transformed target information from the transformation unit 1414. A desired joint state unit 1418 may determine the desired joint states based on the desired tip orientation using inverse kinematics.

In some embodiments, the joint controller 1406 may receive the actual joint state estimates from the actual joint state estimator 1402, receive the desired joint states from the desired joint state generator 1404, and control the joints of the articulatable distal portion 408 based on the actual joint state estimates and desired joint states (e.g., based on a difference between the actual joint state estimates and desired joint states generated by a comparator).

In some embodiments, a proximal output unit 1408 may provide an indication on the proximal end (e.g., the proximal housing) of the medical tool to an operator after detecting that the joints of the articulatable distal portion 408 approach a range of motion limits. In the example of FIG. 13, the proximal output unit 1408 includes a joint motion limit detector 1420. The joint motion limit detector 1420 may detect that the joints of the articulatable distal portion 408 approach a range of motion limits based on actual joint state estimates from the actual joint state estimator 1402 and/or desired joint states from the desired joint state generator 1404. A distal to proximal motion limit mapping unit 1422 may receive the distal joint motion limit detection from the joint motion limit detector 1420, and map the distal joint motion limit (e.g., a motion limit in a first direction) to a proximal end motion limit (e.g., a motion limit in a second direction corresponding to the first direction). A proximal indication unit 1424 may receive the proximal end motion limit from the distal to proximal motion limit mapping unit 1422, and provides an indication to the assistant A on the proximal housing 410 to move the proximal housing 410 of the medical tool 400 based on the proximal end motion limit. In some embodiments, such indication to the assistant A may be provided using an arrangement of lights (e.g., light emitting diode (LED) lights) on the proximal housing 410. Alternatively, the proximal housing 410 may haptically render directional cues to the assistant A. The assistant A may then move the proximal end according to the indication.

Referring to FIGS. 14A, 14B, 15A, and 15B, a comparison between using a conventional imaging tool and an imaging tool (e.g., a tool 400) with an articulatable distal portion is illustrated. FIGS. 14A and 14B illustrate the interference between a conventional imaging tool operated by an assistant and a tool operated by a surgeon and the interference between the assistant and the surgeon when the assistant operates the imaging tool to provide a view of a surgical site for the surgeon from the working direction of the surgeon. As shown in FIGS. 15A and 15B, by using an imaging tool (e.g., a tool 400) with an articulatable distal portion, such interferences are ameliorated by allowing an imaging tool held by the assistant to approach from a direction different from a working direction of the surgeon while still providing a view of a surgical site from the working direction of the surgeon.

Referring to FIG. 14A, illustrated therein is a surgery-type medical environment 1450 substantially similar to the environment 10 of FIG. 1 except for the differences described below. In the surgical environment 1450, an assistant (or some other personnel) A1 standing by the side of a surgeon (or some other personnel) S is holding a proximal housing of a medical tool 1452, where the medical tool 1452 is an endoscopic imaging system. The display system 26 may present images of the surgical site captured by the medical tool 1452. As shown in FIG. 14B, the medical tool 1452 includes a shaft 1454 having a distal end 1453. An imaging device 1455 at the distal end 1453 may provide a view of a surgical site 1462 from a view direction 1460.

To provide a view of a surgical site for the surgeon S aligned with a working direction of the surgeon S, the assistant A1 may occupy the workspace of the surgeon S (e.g., by reaching over in front of the surgeon S and placing hands near/under the surgeon S's arms/chests or around the torso of the surgeon S) to direct the hand-held imaging system to the surgical site in a direction from the surgeon S. This sharing of a common workspace may be inconvenient and uncomfortable, and increasing the possibility of collision between the hand-held imaging system 1452 and the surgeon or between the hand-held imaging system and other tools (e.g., a tool 1456 held by the surgeon S, where the tool 1456 includes a shaft 1458). Further, in such an example, verbal communication between the surgeon S and assistant A1 is needed when the surgeon S requests to change the view.

Referring to FIGS. 15A and 15B, by using an imaging tool (e.g., a tool 400) with an articulatable distal portion, an assistant A1 may stand away from the surgeon S (e.g., opposing the surgeon S), and the imaging tool 400 held by the assistant A1 may approach from a direction different from a working direction of the surgeon S (e.g., holding a tool 1456). As shown in FIG. 15B, an imaging device 454 at a tip 468 of the articulatable distal portion 408 of the imaging tool 400 may provide a view of a surgical site 1462 from a view direction 470. By controlling the articulatable distal portion 408 of the imaging tool 400, the view direction 470 may be adjusted to be the same as the view direction 1460 of FIG. 14B, thereby providing a view of a surgical site from the working direction of the surgeon S. Therefore, by using the imaging tool 400 with an articulatable distal portion, a view of a surgical site from the working direction of the surgeon S may be provided while the imaging tool 400 operated by the assistant A1 approaches the surgical site from another direction.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor-readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read-only memory (ROM), a flash memory, an erasable programmable read-only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
    a medical tool including a shaft having proximal and distal ends and an articulatable distal portion coupled to the distal end of the shaft;
    a processing unit including one or more processors, the processing unit configured to:
        determine a first target in a medical environment, wherein the articulatable distal portion is directed toward the first target;
        determine a first motion of at least a portion of the shaft;
        based on the determined first motion, control a pose of the articulatable distal portion so that the articulatable distal portion remains directed toward the first target;
        in response to a request for transition to a different view direction, control the pose of the articulatable distal portion to direct the articulatable distal portion toward a second target in the medical environment,
        wherein orientations of images captured by an imaging device of the articulatable distal portion during the transition are maintained to be the same regarding a reference including a reference plane or a reference direction by controlling the pose of the articulatable distal portion, and
        wherein a left-to-right order of features in the images is aligned with a first left-to-right reference direction of the reference;
        wherein the first left-to-right reference direction corresponds to a perspective of a first operator who is not controlling the shaft, and wherein the first left-to-right reference direction is different from a second left-to-right reference direction corresponding to a second operator who is controlling the shaft.

2. The system of claim 1, further comprising:
a teleoperational manipulator coupled to the medical tool and configured for control of shaft motion;
a sensor system in communication with the processing unit, the sensor system configured to determine the first motion, wherein the sensor system includes a sensor included in the teleoperational manipulator.

3. The system of claim 1, further comprising:
a teleoperational manipulator coupled to the medical tool and configured for control of shaft motion,
wherein the processing unit is configured to:
based on a command issued for driving the teleoperational manipulator, determine the first motion of the at least a portion of the shaft.

4. The system of claim 1,
wherein the processing unit is further configured to display the images of the first target captured by the imaging device; and wherein the displayed images of the first target are oriented based on the reference.

5. The system of claim 1,
wherein the orientations of images captured by the imaging device are level with the reference plane, and
wherein the reference plane is a horizontal plane or is based on a table top of an operating table of the medical environment.

6. The system of claim 1, wherein the processing unit is further configured to:
determine the reference based on a first image of the first target selected by an operator.

7. The system of claim 1, wherein the images of the first target are upright with respect to the reference direction.

8. The system of claim 1, wherein controlling the pose of the articulatable distal portion includes preserving a roll orientation of a view of the first target with respect to the reference plane.

9. The system of claim 1, further comprising:
a tracking system configured to track at least a portion of an operator's body;
wherein the processing unit is further configured to:
detect a second motion of the at least a portion of the operator's body; and
control the pose of the articulatable distal portion in response to the detected second motion of the at least a portion of the operator's body.

10. The system of claim 1, wherein the processing unit is further configured to: determine whether an operator has performed a distal orientation adjustment request, and
wherein controlling the pose of the articulatable distal portion is further based on a determination that the operator has performed the distal orientation adjustment request.

11. The system of claim 1, wherein controlling the pose of the articulatable distal portion includes controlling an orientation or a translation of the articulatable distal portion.

12. The system of claim 1, further comprising:
a sensor system coupled to the distal end of the shaft and in communication with the processing unit, the sensor system includes an imaging device for capturing images of the first target.

13. The system of claim 1, wherein the medical tool includes a proximal housing configured for manual control of shaft motion.

14. The system of claim 1, wherein the processing unit is further configured to:
determine the first target based on an input provided by an operator.

15. The system of claim 1, wherein the medical tool includes an imaging device for capturing images of the first target, and
wherein the processing unit is further configured to:
process the images to determine a location of the first target.

16. The system of claim 1, wherein the processing unit is further configured to:
determine that the articulatable distal portion reaches a motion limit, and
provide, using a proximal housing located at the proximal end, an indication to an operator for moving the proximal housing in a direction corresponding to the motion limit.

* * * * *

UNITED STATES PATENT AND TRADEMARK OFFICE
CERTIFICATE OF CORRECTION

PATENT NO. : 11,992,283 B2
APPLICATION NO. : 16/489735
DATED : May 28, 2024
INVENTOR(S) : Brandon D. Itkowitz and David W. Robinson Page 1 of 1

It is certified that error appears in the above-identified patent and that said Letters Patent is hereby corrected as shown below:

In the Specification

Column 1, Lines 8 - 13 Please replace first paragraph to read as follows:
-- This patent application is the U.S. national phase of International Application No. PCT/US2018/021373, filed March 7, 2018, which designated the U.S. and claims priority to and benefit of the filing date of U.S. Provisional Patent Application 62/468,097, entitled "SYSTEMS AND METHODS FOR CONTROLLING MEDICAL TOOL WITH ARTICULATABLE DISTAL PORTION," filed March 7, 2017, which is hereby incorporated by reference herein in their entirety. --

Signed and Sealed this
Twenty-seventh Day of August, 2024

Katherine Kelly Vidal
*Director of the United States Patent and Trademark Office*